United States Patent
Amanai et al.

(10) Patent No.: US 10,620,426 B2
(45) Date of Patent: Apr. 14, 2020

(54) IMAGE PICKUP APPARATUS AND CAPSULE ENDOSCOPE

(71) Applicant: OLYMPUS CORPORATION, Hachioji-shi, Tokyo (JP)

(72) Inventors: Takahiro Amanai, Hachioji (JP); Ayami Imamura, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 219 days.

(21) Appl. No.: 15/392,368

(22) Filed: Dec. 28, 2016

(65) Prior Publication Data

US 2017/0219813 A1 Aug. 3, 2017

(30) Foreign Application Priority Data

Jan. 28, 2016 (JP) ................. 2016-014629

(51) Int. Cl.
*A61B 1/05* (2006.01)
*A61B 1/04* (2006.01)
(Continued)

(52) U.S. Cl.
CPC ............ *G02B 23/2438* (2013.01); *A61B 1/05* (2013.01); *A61B 1/051* (2013.01);
(Continued)

(58) Field of Classification Search
CPC ............ G02B 23/2438; G02B 23/2461; G02B 23/2484; G02B 27/4211; G02B 27/0075;
(Continued)

(56) References Cited

U.S. PATENT DOCUMENTS

2003/0214726 A1* 11/2003 Mihara .................. G02B 13/04
359/676
2004/0130798 A1 7/2004 Zhang et al.
(Continued)

FOREIGN PATENT DOCUMENTS

JP H08508116 A 8/1996
JP 2012515436 A 7/2012
(Continued)

OTHER PUBLICATIONS

Japanese Office Action dated Jul. 31, 2019 (and English translation thereof) issued in counterpart Japanese Application No. 2016-014629.
(Continued)

*Primary Examiner* — Timothy J Neal
*Assistant Examiner* — William B Chou
(74) *Attorney, Agent, or Firm* — Holtz, Holtz & Volek PC

(57) ABSTRACT

An image pickup apparatus includes an image forming optical system which includes an aperture stop that sets an axial light beam, and a diffracting optical surface disposed at a position different from a position where the aperture stop is disposed, and an imager which is disposed on an image side of the image forming optical system, and has a light-receiving surface which is not flat and is curved to be concave toward the image forming optical system, wherein the diffracting optical surface satisfies the following conditional expression (1).

$$0.1 < |DSD/TL| \leq 1.0 \qquad (1)$$

where,
TL denotes an actual distance on an optical axis of the image forming optical system, from a surface of incidence of the image forming optical system up to the light-receiving surface,
DSD denotes an actual distance on the optical axis of the image forming optical system, from a position of the aperture stop up to the diffracting optical surface, and
when a focal length of the image forming optical system is variable, conditional expression (1) is a conditional expression in a state at a wide angle end.

13 Claims, 22 Drawing Sheets

(51) Int. Cl.
*G02B 23/24* (2006.01)
*G02B 27/42* (2006.01)
*G02B 15/20* (2006.01)

(52) U.S. Cl.
CPC ..... *G02B 23/2461* (2013.01); *G02B 23/2484* (2013.01); *G02B 27/4211* (2013.01); *A61B 1/041* (2013.01); *A61B 2562/162* (2013.01); *A61B 2562/164* (2013.01); *A61B 2562/166* (2013.01); *G02B 15/20* (2013.01)

(58) Field of Classification Search
CPC ........... G02B 15/20; A61B 1/05; A61B 1/051; A61B 1/041; A61B 2562/162; A61B 2562/164; A61B 2562/166
See application file for complete search history.

(56) References Cited

U.S. PATENT DOCUMENTS

| | | | | |
|---|---|---|---|---|
| 2005/0030408 | A1* | 2/2005 | Ito | H04N 5/2253 348/340 |
| 2005/0124858 | A1* | 6/2005 | Matsuzawa | A61B 1/00096 600/176 |
| 2005/0259335 | A1* | 11/2005 | Nishioka | G02B 26/0825 359/726 |
| 2006/0209292 | A1* | 9/2006 | Dowski, Jr. et al. | 356/121 |
| 2009/0234448 | A1* | 9/2009 | Weeber et al. | A61F 2/16 623/6.3 |
| 2012/0016199 | A1* | 1/2012 | Baba | A61B 1/00096 600/109 |
| 2013/0316487 | A1* | 11/2013 | de Graff | H01L 27/14683 438/66 |
| 2014/0185144 | A1* | 7/2014 | Kubota | G02B 13/16 359/680 |
| 2016/0216494 | A1* | 7/2016 | Shiokawa | G02B 13/16 |
| 2017/0020393 | A1* | 1/2017 | Rentschler et al. | A61B 5/0084 |
| 2017/0261726 | A1 | 9/2017 | Sekine | |
| 2017/0293116 | A1 | 10/2017 | Matsumoto | |
| 2017/0347867 | A1* | 12/2017 | Sato | G02B 23/2438 |

FOREIGN PATENT DOCUMENTS

| | | |
|---|---|---|
| WO | 9518393 A1 | 7/1995 |
| WO | 2010081137 A2 | 7/2010 |
| WO | 2013027516 A1 | 2/2013 |
| WO | 2016084117 A1 | 6/2016 |
| WO | 2016110883 A1 | 7/2016 |

OTHER PUBLICATIONS

English-language translation of WO 2013/027516.

* cited by examiner

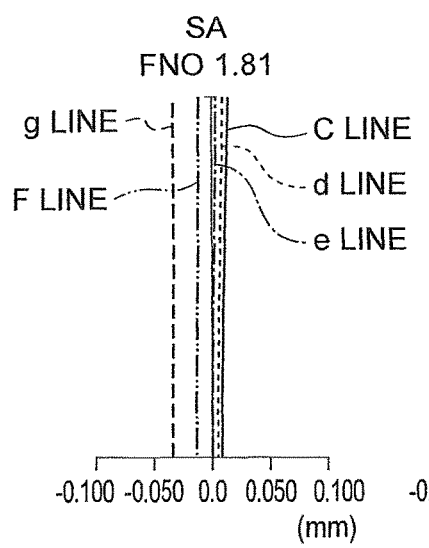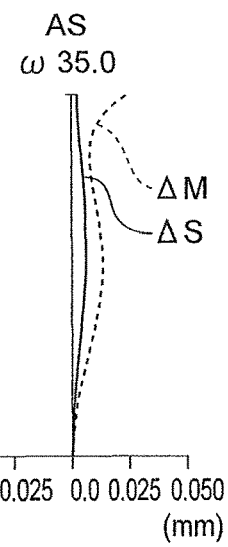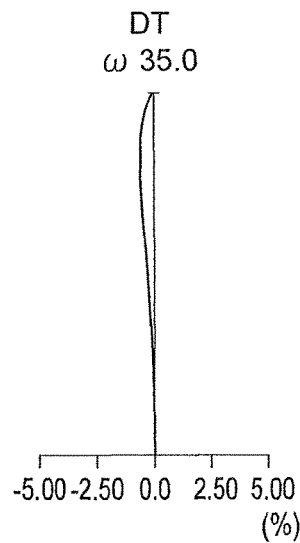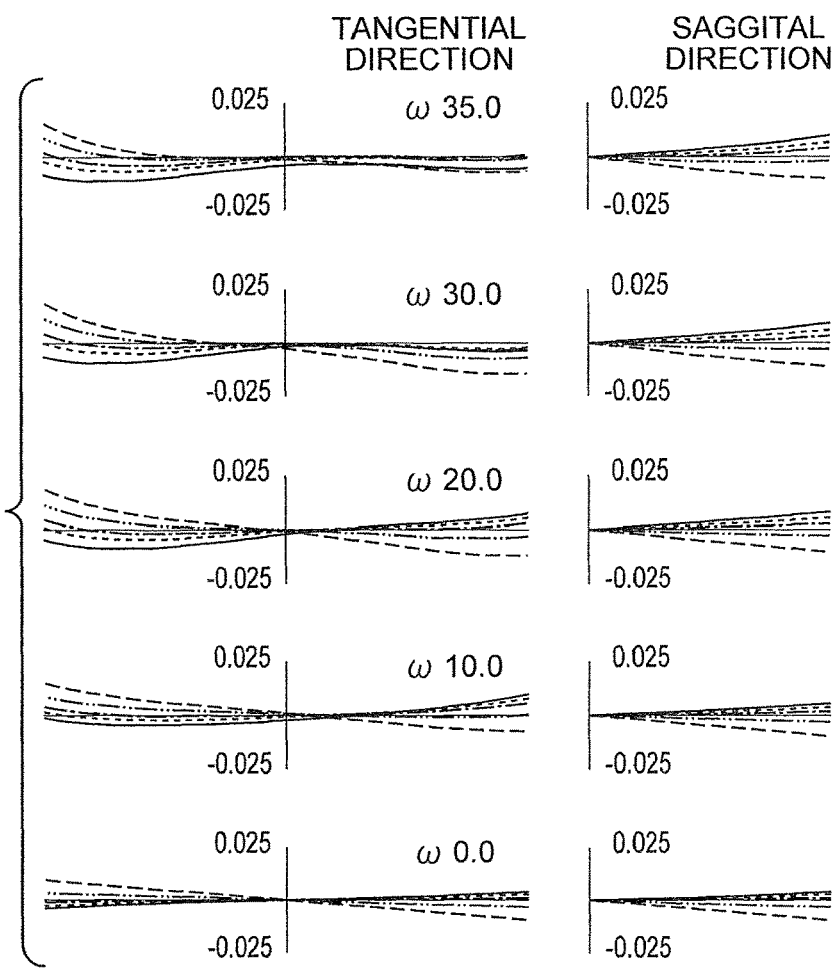

SA
FNO 1.81

-0.100 -0.050 0.0 0.050 0.100
(mm)

AS
ω 35.0

-0.050 -0.025 0.0 0.025 0.050
(mm)

DT
ω 35.0

-5.00 -2.50 0.0 2.50 5.00
(%)

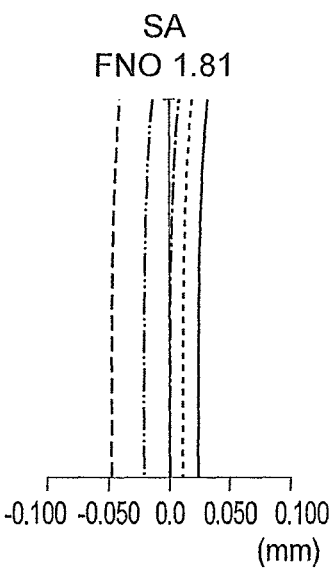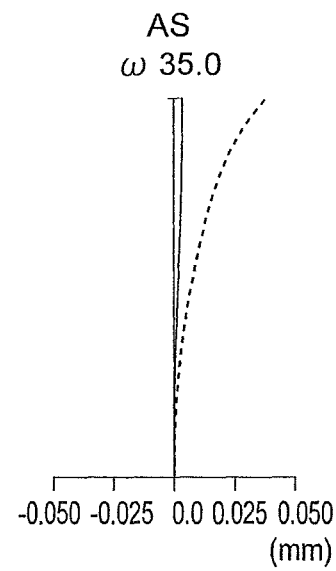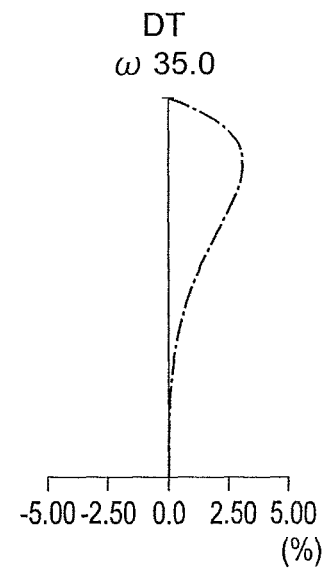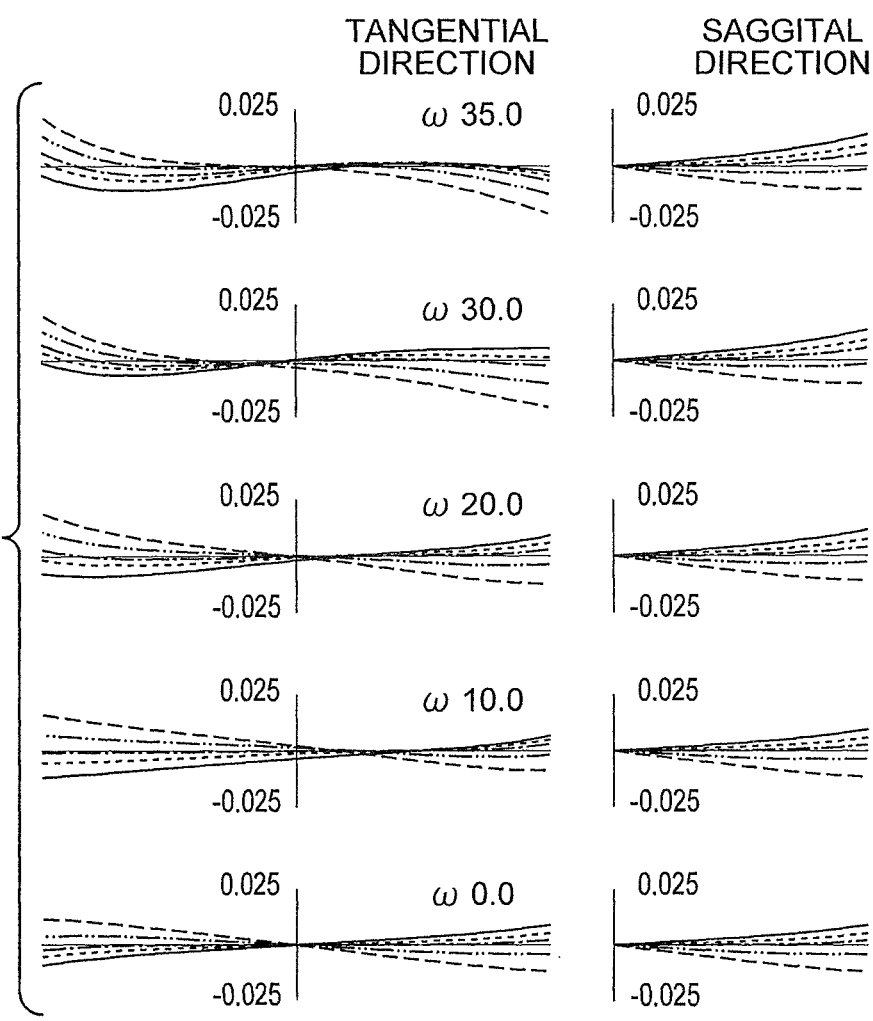

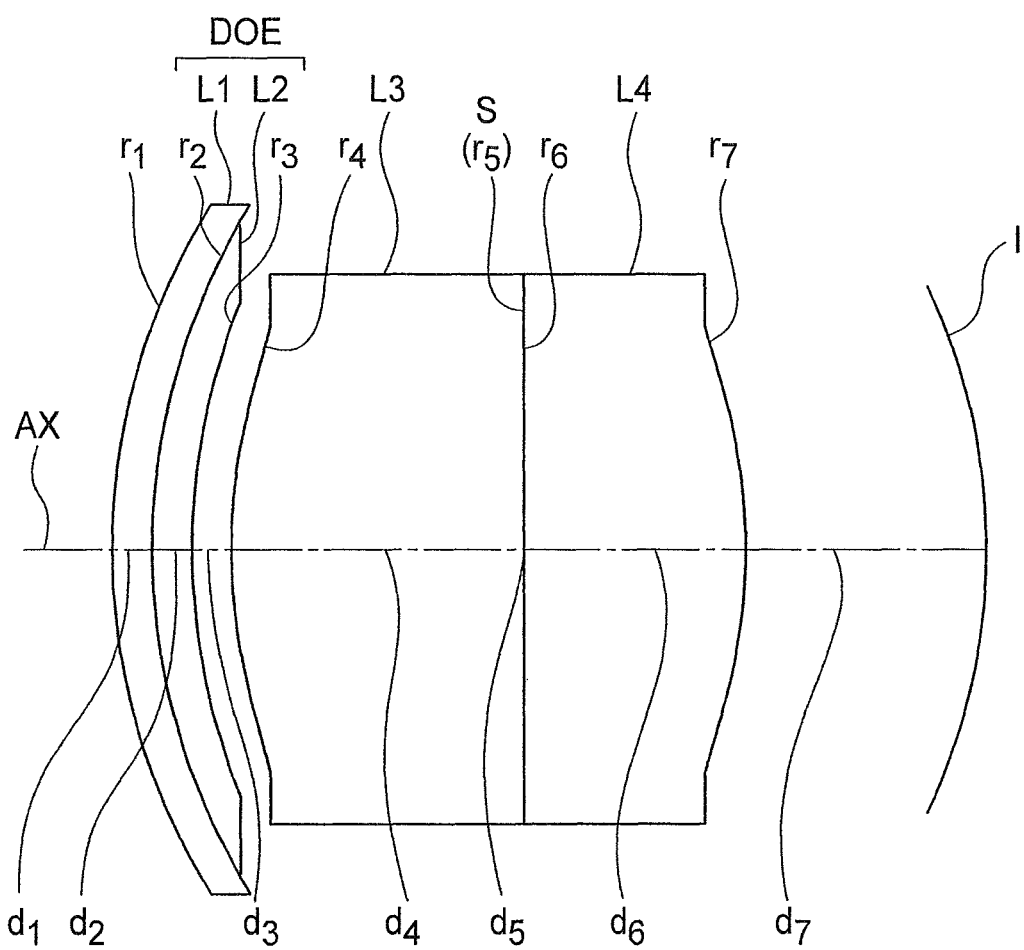

SA
FNO 1.8

AS
ω 35.0

DT
ω 35.0

SA
FNO 3.473

AS
ω 81.0

DT
ω 81.0

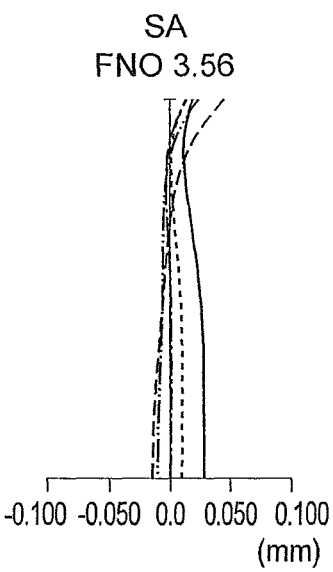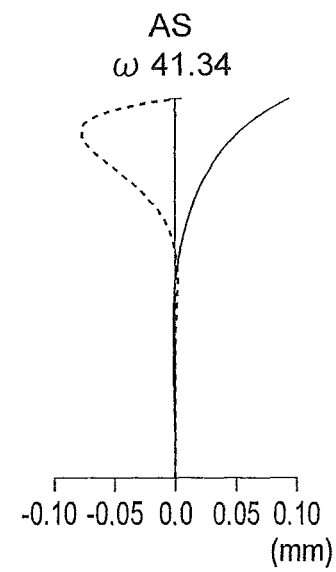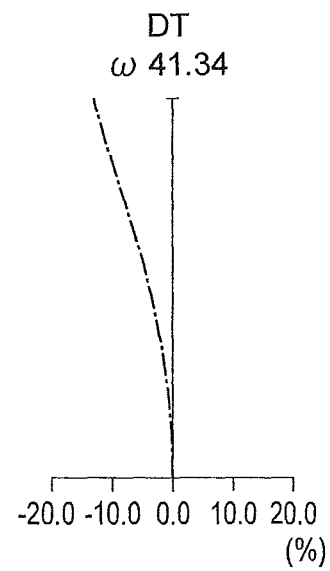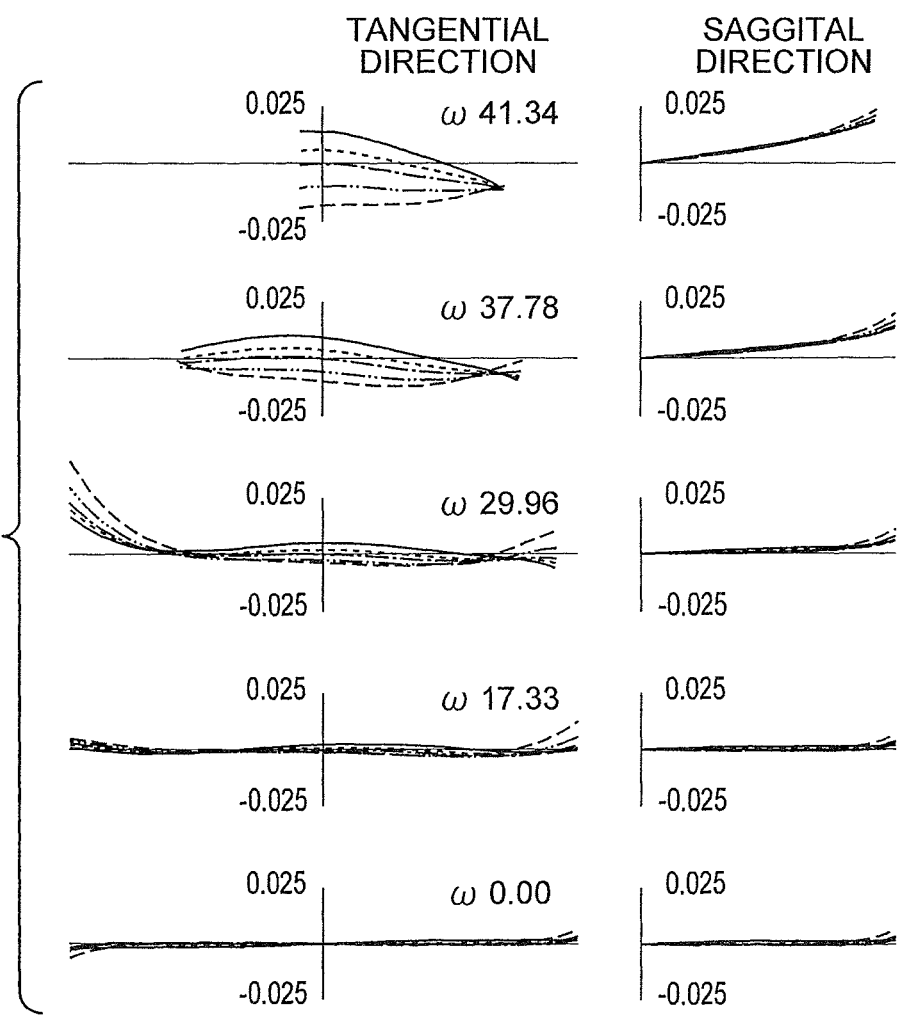

SA
FNO 4.68

AS
ω 21.35

DT
ω 21.35

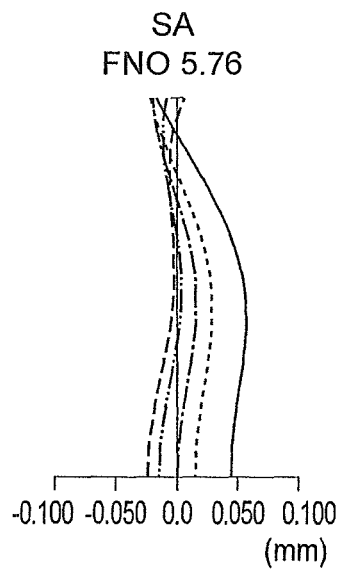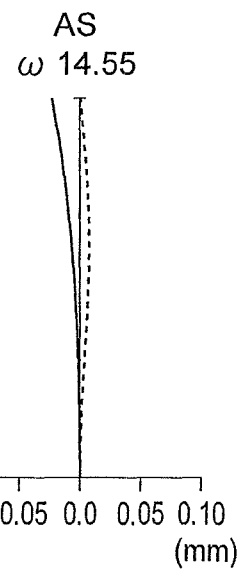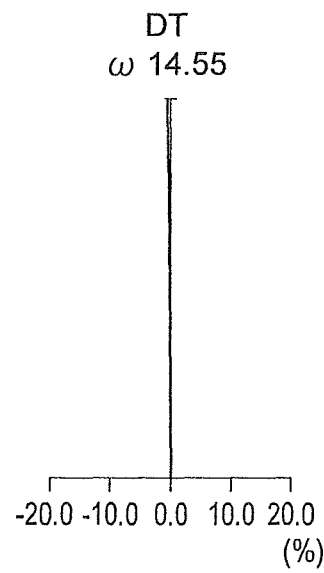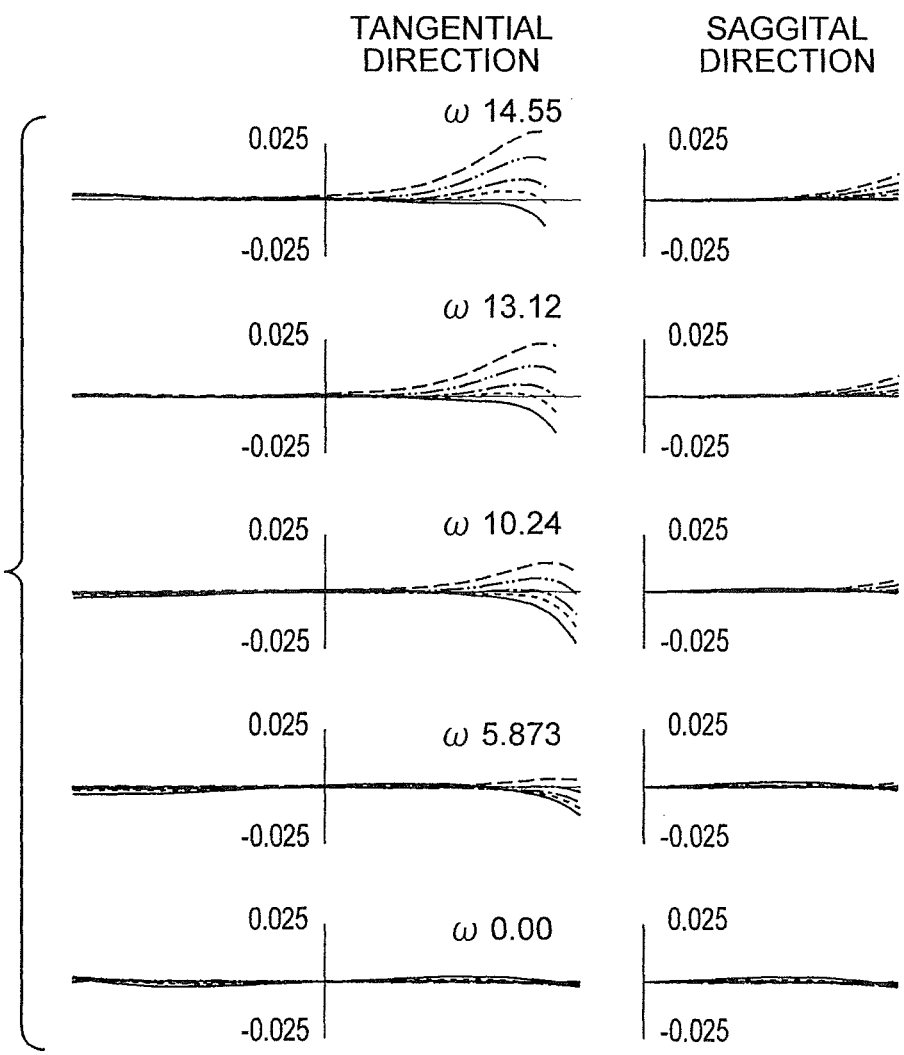

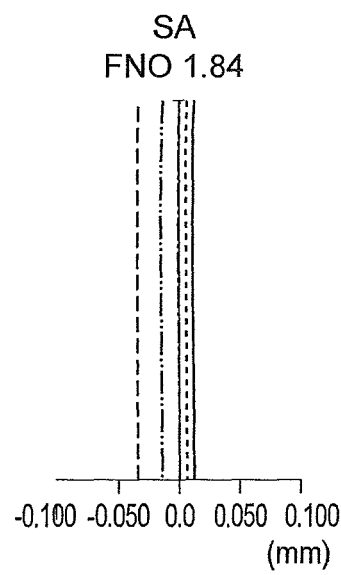
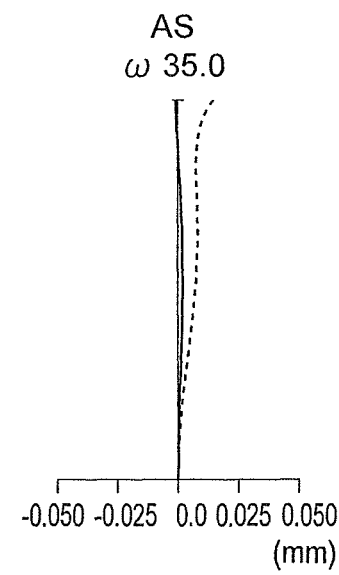
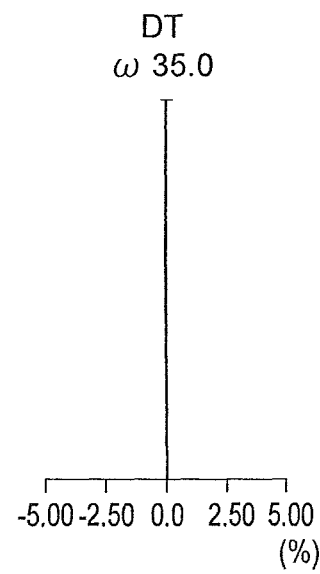
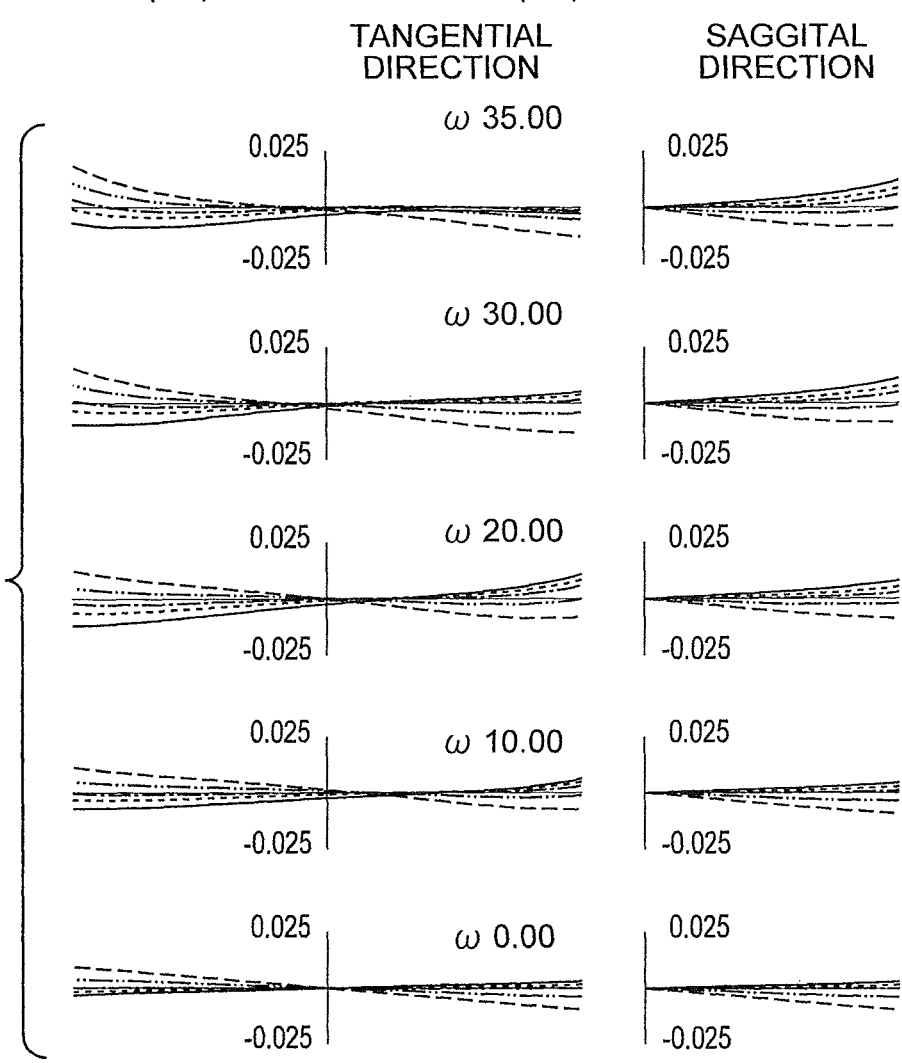

IMAGE PICKUP APPARATUS AND CAPSULE ENDOSCOPE

CROSS-REFERENCE TO RELATED APPLICATION

The present application is based upon and claims the benefit of priority from the prior Japanese Patent Application No. 2016-014629 filed on Jan. 28, 2016; the entire contents of which are incorporated herein by reference

BACKGROUND OF THE INVENTION

Field of the Invention

The present invention relates to an image pickup apparatus and a capsule endoscope.

Description of the Related Art

As an optical system having a wide angle of view, which forms a curved image, a zoom lens and an image pickup apparatus have been proposed in International Unexamined Patent Application Publication No. 2013/027516. In this image pickup apparatus, by using an image pickup element having a light-receiving surface (an image pickup surface) of which a spherical concave surface is directed toward an object side, Petzval's sum is in acceptable range, and a degree of freedom of selecting a glass material is improved.

SUMMARY OF THE INVENTION

An image pickup apparatus according to at least some of the embodiments of the present invention includes an image forming optical system which includes an aperture stop that sets an axial light beam, and a diffracting optical surface disposed at a position different from a position where the aperture stop is disposed, and an imager which is disposed on an image side of the image forming optical system, and has a light-receiving surface which is not flat and is curved to be concave toward the image forming optical system, wherein the diffracting optical surface satisfies the following conditional expression (1).

$$0.1 < |DSD/TL| \leq 1.0 \quad (1)$$

where,

TL denotes a practical distance on an optical axis of the image forming optical system, from a surface of incidence of the image forming optical system up to the light-receiving surface, DSD denotes a practical distance on the optical axis of the image forming optical system, from a position of the aperture stop up to the diffracting optical surface, and when a focal length of the image forming optical system is variable, conditional expression (1) is a conditional expression in a state at a wide angle end.

Moreover, an image pickup apparatus according to some of the embodiments of the present invention includes an image forming optical system which includes an aperture stop that sets an axial light beam, and a diffracting optical surface disposed at a position different from a position where the aperture stop is disposed, and an imager which is disposed on an image side of the image forming optical system, and has a light-receiving surface which is not flat and is curved to be concave toward the image forming optical system, wherein there is an optical surface which is not flat, between the aperture stop and the diffracting optical surface.

Moreover, an image pickup apparatus according to at least some of the embodiments of the present invention includes an image forming optical system which includes an aperture stop that sets an axial light beam, and a diffracting optical surface disposed at a position different from a position where the aperture stop is disposed, and an imager which is disposed on an image side of the image forming optical system, and has a light-receiving surface which is not flat and is curved to be concave toward the image forming optical system, wherein there is a positive lens between the aperture stop and the diffracting optical surface.

Moreover, an image pickup apparatus according to at least some of the embodiments of the present invention includes an image forming optical system which includes an aperture stop that sets an axial light beam, and a diffracting optical surface disposed at a position different from a position where the aperture stop is disposed, and an imager which is disposed on an image side of the image forming optical system, and has a light-receiving surface which is not flat and is curved to be concave toward the image forming optical system, wherein the diffracting optical surface is formed to be concave toward the aperture stop.

Moreover, an image pickup apparatus according to at least some of the embodiments of the present invention includes an image forming optical system which includes an aperture stop that sets an axial light beam, and a diffracting optical surface disposed at a position different from a position where the aperture stop is disposed, and an imager which is disposed on an image side of the image forming optical system, and has a light-receiving surface which is not flat and is curved to be concave toward the image forming optical system, wherein there is an air space between the aperture stop and the diffracting optical surface.

Moreover, a capsule endoscope according to at least some of the embodiments of the present invention includes the abovementioned image pickup apparatus, an illuminating unit, and a cover portion having a dome shape disposed on an object side of both the image forming optical system and the illuminating unit.

BRIEF DESCRIPTION OF THE DRAWING

FIG. 2A, FIG. 2B, FIG. 2C, and FIG. 2D are aberration diagrams of the image pickup apparatus according to the example 1;

FIG. 6A, FIG. 63, FIG. 6C, and FIG. 6D are aberration diagrams of the image pickup apparatus according to the example 3;

FIG. 7 is a cross-sectional view of an image pickup apparatus according to an example 4 of the present invention;

FIG. 11A is a cross-sectional view in a state at a wide angle end, FIG. 11B is a cross-sectional view in an intermediate focal length state, and FIG. 11C is a cross-sectional view in a state at a telephoto end;

FIG. 12A, FIG. 12B, FIG. 12C, and FIG. 12D are aberration diagrams of the image pickup apparatus according to the example 6;

FIG. 14A, FIG. 14B, FIG. 14C, and FIG. 14D are aberration diagrams of the state at the telephoto end of the image pickup apparatus according to the example 6;

FIG. 16A, FIG. 16B, FIG. 16C, and FIG. 16D are aberration diagrams of the image pickup apparatus according to the example 7;

FIG. 21A is a diagram showing an example of a car-mounted camera mounted at an outside of a car, and FIG. 21B is a diagram showing an example of a car-mounted camera mounted inside the car.

DETAILED DESCRIPTION OF THE INVENTION

Figure 1:
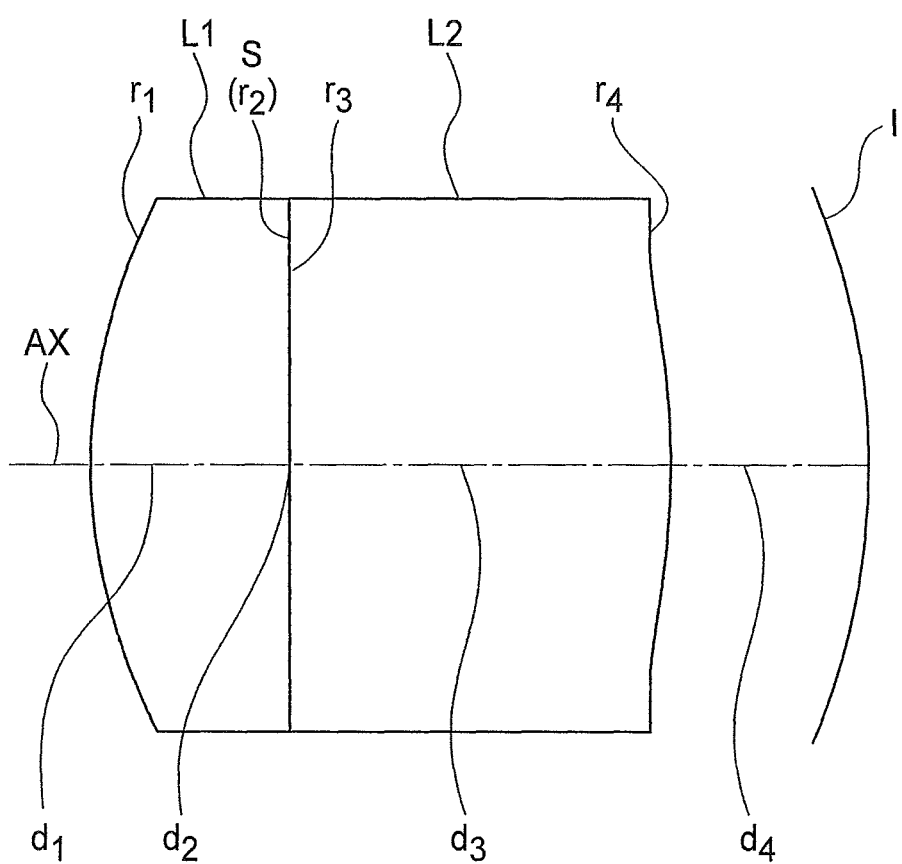
FIG. 1 is a cross-sectional view of an image pickup apparatus according to an example 1 of the present invention.

Exemplary embodiments and examples of an image pickup apparatus and a capsule endoscope according to the present invention will be described below in detail by referring to the accompanying diagrams. However, the present invention is not limited to the embodiments and examples described below.

An image pickup apparatus according to a first embodiment of the present invention includes an image forming optical system which includes an aperture stop that sets an axial light beam, and a diffracting optical surface disposed at a position different from a position where the aperture stop is disposed, and an imager which is disposed on an image side of the image forming optical system, and has a light-receiving surface which is not flat and is curved to be concave toward the image forming optical system, wherein the diffracting optical surface satisfies the following conditional expression (1).

$$0.1 < |DSD/TL| \leq 1.0 \qquad (1)$$

where,

TL denotes an actual distance on an optical axis of the image forming optical system, from a surface of incidence of the image forming optical system up to the light-receiving surface, DSD denotes an actual distance on the optical axis of the image forming optical system, from a position of the aperture stop up to the diffracting optical surface, and when a focal length of the image forming optical system is variable, conditional expression (1) is a conditional expression in a state at a wide angle end.

In a case in which, the aperture stop is to be disposed nearest to a side of incidence of the image forming optical system, an opening of the aperture stop is let to be a surface of incidence.

In the image pickup apparatus according to the present embodiment, by using the imager having the light-receiving surface which is not flat and is curved to be concave toward the image forming optical system, an occurrence of a curvature of field in the image forming optical system is in acceptable range, and there is no need to make Petzval's sum of the optical system small. Moreover, using the diffracting optical surface is advantageous for correction of a chromatic aberration.

Moreover, in the present embodiment, it is possible to keep the position of the diffracting optical surface away from the position where the aperture stop is disposed, by a certain distance. Therefore, it is possible to dispose the diffracting optical surface at a position where principal light rays for respective image heights are separated spatially. Accordingly, it is possible to form a shape of the diffracting optical surface to be suitable for an angle of incidence of the principal light ray of each image height, and to reduce light of unnecessary order that is generated depending on an angle of incidence of a light ray incident on the diffracting optical surface.

In the following description, an element that has the diffracting optical surface will be referred to as a diffractive optical element DOE. In each of the examples to be described later, the diffractive optical element DOE will be specified clearly.

For the position of the diffracting optical surface, it is significant to satisfy conditional expression (1). Conditional expression (1) regulates an appropriate ratio of the above-mentioned DSD and TL.

An upper limit value of conditional expression (1) cannot be exceeded.

By making an arrangement such that a value does not fall below a lower limit value of conditional expression (1), it is possible to separate positions of the principal light rays at respective image heights incident on the diffracting optical surface.

For the diffracting optical surface, by separating positions of the principal light rays of respective image heights, it is possible to optimize a shape of the diffracting optical surface according to the angle of incidence of the principal light ray of each height. For instance, with regard to an axial principal light ray and an off-axis principal light ray, it is possible to carry out setting of an angle of a saw-tooth shape of the diffracting optical surface according to the angle of incidence of the principal light ray of each image height.

Accordingly, it is possible to make an arrangement to reduce the light of unnecessary order that is generated depending on the angle of incidence of a light ray incident on the diffracting optical surface.

According to such arrangement, it is possible to reduce an aberration by a shape of the light-receiving surface having an arrangement other than lenses and a diffracting optical surface that has almost no thickness practically. Moreover, by keeping the position of the diffracting optical surface away from the aperture stop by a certain distance, it is possible to separate the axial principal light ray and the off-axis principal light ray on the diffracting optical surface. This is advantageous for reducing the generation of the light of unnecessary diffraction order. Consequently, it is easy to carry out reduction in the number of lenses and small-sizing, thereby achieving an image pickup apparatus which includes an image forming optical system that enables to achieve a favorable optical performance.

Unlike in the present embodiment, when the diffracting optical surface and the aperture stop are excessively close, the axial principal light ray passes through an area near a center of the diffracting optical surface, and an angle of incidence of the off-axis principal light ray on the diffracting optical surface becomes large. When the diffracting optical surface is optimized for the axial principal light ray, generation of the light of unnecessary diffraction order becomes substantial in an optical path of an off-axis light beam, and a problem of degradation of image quality arises. Particularly, in a case of a diffractive optical element DOE made of two layers as it will be described later, since a difference in refractive indices of the layers becomes small, it is necessary to increase a depth of a pitch of the saw-tooth shape for generating a phase difference. As a result, even for a principal light ray at a position shifted slightly in a different direction from the optical axis toward the off-axis direction, the light of unnecessary diffraction order is generated, and the image quality is susceptible to be degraded due to flare.

In a case of the present embodiment, the degree of freedom of forming the shape of the diffracting optical surface to be optimum for each image height becomes high. Accordingly, it is possible to suppress generation of unnecessary diffraction order light at the diffracting optical surface.

Moreover, preferable embodiments of the present invention will be described below. When the position of the diffracting optical surface is excessively close to the image plane, a focal length of a diffractive optical element having the diffracting optical surface becomes excessively short. Accordingly, a pitch of the diffracting optical surface becomes fine, thereby giving rise to a problem that becomes an issue in manufacturing, and furthermore, generation of the unnecessary diffraction order light becomes another issue. Therefore, it is preferable that the diffracting optical surface is disposed at a position different from a position of the light-receiving surface.

It is preferable that the diffracting optical surface and the light-receiving surface are disposed with an air space sandwiched between the two.

Even in the embodiments to be described later, it is effective that the abovementioned arrangements are satisfied simultaneously.

Moreover, it is preferable to satisfy mutually the arrangement of the abovementioned embodiment and arrangement of the embodiments to be described later, simultaneously.

Moreover, an image pickup apparatus according to a second embodiment of the present invention includes an image forming optical system which includes an aperture stop that sets an axial light beam, and a diffracting optical surface disposed at a position different from a position where the aperture stop is disposed, and an imager which is disposed on an image side of the image forming optical system, and has a light-receiving surface which is not flat and is curved to be concave toward the image forming optical system, wherein there is an optical surface which is not flat, between the aperture stop and the diffracting optical surface.

Repetitive description of the similar arrangement described above will be omitted. In the image pickup apparatus of the present embodiment, by using the imager including the light-receiving surface which is not flat and is curved to be concave toward the image forming optical system, the occurrence of the curvature of field in the image forming optical system is in acceptable range, and there is no need to make Petzval's sum of the optical system small. Moreover, using the diffracting optical surface is advantageous for correcting of the chromatic aberration.

Furthermore, the optical surface of the present embodiment which is not flat, due to an optical effect, is advantageous for separating further the positions of the principal light rays at the diffracting optical surface. Accordingly, in the present embodiment, it is possible to make the principal light rays of respective image heights to be incident on the diffracting optical surface in a state of being further separated spatially. As a result, it is possible to form a shape of the diffracting optical surface and the diffractive optical element DOE to be appropriate for each image height. For instance, with regard to an axial principal light ray and an off-axis principal light ray, it is possible to set an angle of a saw-tooth shape of the diffracting optical surface according to the angle of incidence of the principal light ray of each image height.

According to such arrangements, it is possible to reduce an aberration by the shape of the light receiving surface having an arrangement other than lenses and the diffracting optical surface that has almost no thickness practically. Moreover, by disposing the optical surface which is not flat, between the aperture stop and the diffracting optical surface, it is possible to separate the axial principal light ray and the off-axis principal light ray on the diffracting optical surface. This is advantageous for reducing the generation of the light of unnecessary diffraction order. Consequently, it is easy to carry out reduction in the number of lenses and small-sizing, thereby achieving an image pickup apparatus which includes an image forming optical system that enables to achieve a favorable optical performance.

Moreover, an image pickup apparatus according to a third embodiment of the present invention includes an image forming optical system which includes an aperture stop that sets an axial light beam, and a diffracting optical surface disposed at a position different from a position where the aperture stop is disposed, and an imager which is disposed on an image side of the image forming optical system, and has a light-receiving surface which is not flat and is curved to be concave toward the image forming optical system, wherein there is a positive lens between the aperture stop and the diffracting optical surface.

Repetitive description of the similar arrangement described above will be omitted. When there is a positive lens between the aperture stop and the diffracting optical surface, it is possible to focus a light beam including the principal light rays of respective image heights by the positive lens, and to make the light beam including the principal light rays of respective image heights be incident on the diffracting optical surface, in a state of being further separated. Accordingly, it becomes easy to form the shape of the diffracting optical surface to be appropriate for an angle of incidence of the principal light ray of each image height, which is advantageous for reducing the generation of the light of unnecessary diffraction order. Consequently, it is easy to carry out reduction in the number of lenses and small-sizing, thereby achieving an image pickup apparatus which includes an image forming optical system that enables to achieve a favorable optical performance.

Moreover, an image pickup apparatus according to a fourth embodiment of the present invention includes an image forming optical system which includes an aperture stop that sets an axial light beam, and a diffracting optical surface disposed at a position different from a position where the aperture stop is disposed, and an imager which is disposed on an image side of the image forming optical system, and has a light-receiving surface which is not flat and is curved to be concave toward the image forming optical system, wherein the diffracting optical surface is formed to be concave toward the aperture stop.

Repetitive description of the similar arrangement described above will be omitted. The principal light ray is incident on the image forming optical system with the position of the aperture stop as a center. Therefore, by forming the diffracting optical surface to be concave toward the aperture stop, it is possible to make the principal light ray of any image height be incident nearly perpendicularly on the diffracting optical surface, which is advantageous for improving an efficiency of diffraction. Accordingly, it is possible to suppress the generation of unnecessary diffraction order light at the diffracting optical surface. Consequently, it is easy to carry out reduction in the number of lenses and small-sizing, thereby achieving an image pickup apparatus which includes an image forming optical system that enables to achieve a favorable optical performance.

Moreover, according to a preferable aspect of the present embodiment, it is desirable that the image pickup apparatus satisfies the following conditional expression (2).

$$0.1 < |f/R_{doe}| < 0.8 \quad (2)$$

where, f denotes a focal length of the image forming optical system, $R_{doe}$ denotes a radius of curvature of a virtual spherical surface including a surface apex and a point at which a principal light ray with the maximum image height of the image forming optical system and the diffracting optical surface intersect, when a point of intersection of the optical axis and the diffracting optical surface is let to be the surface apex, and when the focal length of the image forming optical system is variable, conditional expression (2) is a conditional expression in a state at a wide angle end.

Conditional expression (2) regulates an appropriate ratio of the focal length of the image forming optical system and the abovementioned $R_{doe}$.

By satisfying conditional expression (2), it is possible to arrange the diffracting optical surface such that the principal light ray of each image height is incident nearly perpendicularly by the diffracting optical surface.

It is preferable to let an upper limit value of conditional expression (2) to be 0.5 and a lower limit value of conditional expression (2) to be 0.2.

Moreover, according to a preferable aspect of each embodiment, it is desirable that the diffracting optical surface is disposed at any position on a lens surface nearest to image of the image forming optical system up to the light-receiving surface, and the image pickup apparatus further satisfies the following conditional expression (3).

$$0.0 \leq |\sin \theta_{doe} - \sin \theta_{img}| < 0.1 \quad (3)$$

where, $\theta_{doe}$ denotes an angle with respect to an optical axis of a virtual line connecting a point at which a principal light ray with the maximum image height of the image forming optical system and the diffracting optical surface intersect, and a center of curvature of the diffracting optical surface, $\theta_{img}$ denotes an angle with respect to an optical axis of a virtual line connecting a point at which the principal light ray with the maximum image height of the image forming optical system and the light-receiving surface intersect, and a center of curvature of the light-receiving surface, and when the focal length of the image forming optical system is variable, conditional expression (3) is a conditional expression in a state at the wide angle end.

Here, the 'center of curvature of the diffracting optical surface' refers to a center of curvature of the diffracting optical surface of a paraxial area, and the 'center of curvature of the light-receiving surface' refers to a center of curvature of a virtual surface including the apex point and a point at which the principal light ray of the maximum image height of the image forming optical system and the light receiving surface intersect.

Figure 22A:
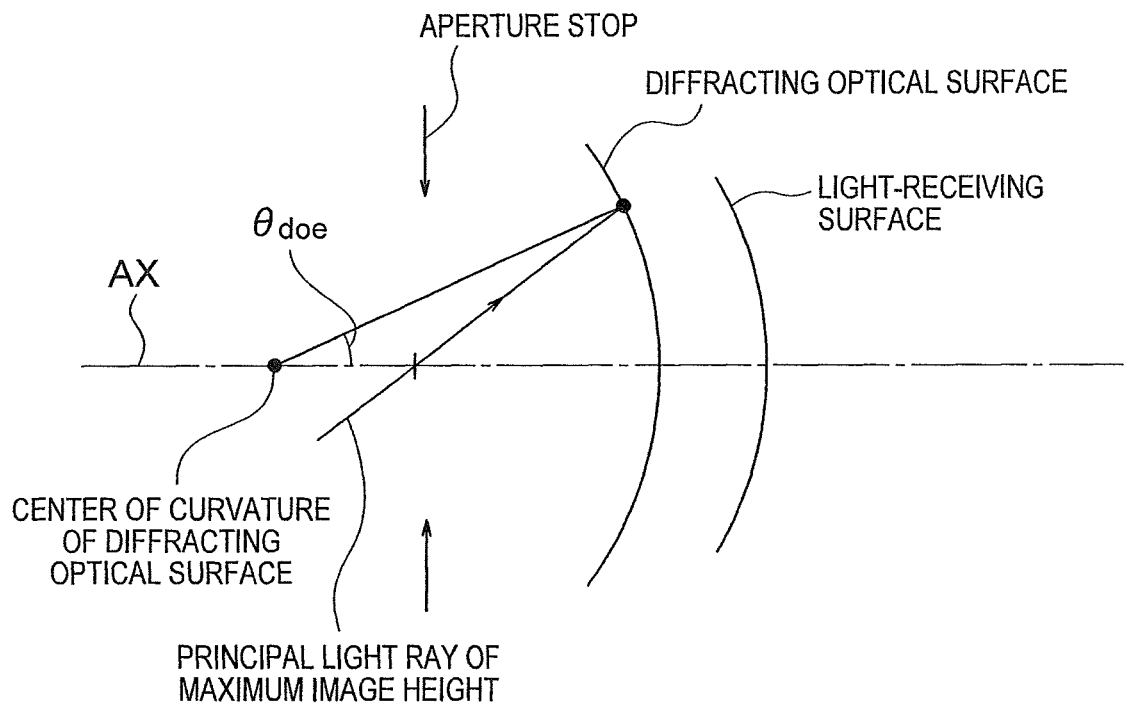
FIG. 22A and FIG. 22B are diagrams for explaining parameters.
Figure 22B:
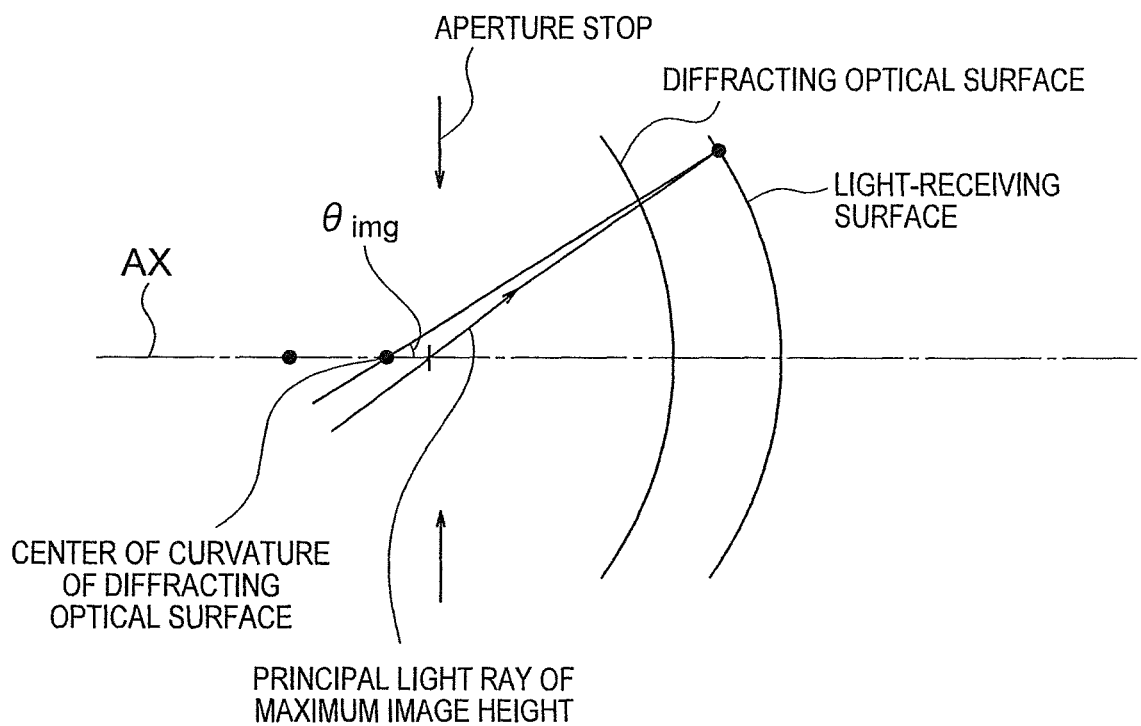

FIG. 22A and FIG. 22B are diagrams explaining the parameters $\theta_{doe}$ and $\theta_{img}$.

Conditional expression (3) regulates an appropriate relationship of the abovementioned $\theta_{doe}$ and $\theta_{img}$.

By satisfying conditional expression (3), it is possible to form the diffracting optical surface such that the principal light ray of each image height is incident nearly perpendicularly on the diffracting optical surface.

Moreover, in a case of not satisfying conditional expression (3), the principal light ray is incident to be substantially inclined on the diffracting optical surface. Consequently, either there is a degradation of image quality due to the unnecessary diffraction order light or the principal light ray is excessively inclined with respect to the light-receiving surface, and the image quality is susceptible to be degraded due to shading.

It is preferable to let an upper limit value of conditional expression (3) to be 0.05.

Moreover, according to another embodiment, an image pickup apparatus includes an image forming optical system which includes an aperture stop that sets an axial light beam, and a diffracting optical surface disposed at a position different from a position where the aperture stop is disposed, and an imager which is disposed on an image side of the image forming optical system, and has a light-receiving surface which is not flat and is curved to be concave toward the image forming optical system, wherein there is an air space between the aperture stop and the diffracting optical surface.

Repetitive description of the similar arrangement described above will be omitted. By separating the diffracting optical surface and the aperture stop by sandwiching the air space, it is possible to separate the principal light rays of respective image heights incident on the diffracting optical surface.

Moreover, by disposing the diffracting optical surface sandwiching the air space with a lens in the image forming optical system, it is possible to adjust independently a shape of each of the lens and the diffractive optical element DOE having the diffracting optical surface. It is preferable since the shape of a lens surface can be optimized for correction of an aberration other than the chromatic aberration. Consequently, it is easy to carry out reduction in the number of lenses and small-sizing, thereby achieving an image pickup apparatus which includes an image forming optical system that enables to achieve a favorable optical performance.

Moreover, according to a preferable aspect of each embodiment, it is desirable that the image forming optical system includes at least one aspheric surface.

By including the aspheric surface, it is possible to correct favorably, a monochromatic spherical aberration, a coma, and an astigmatic difference.

Moreover, according to a preferable aspect of each embodiment, it is desirable that out of lens surfaces in the image forming optical system, a surface nearest to image is a surface which is convex toward the image side.

Here, the diffractive optical element DOE is not included in 'lenses'.

By letting the surface nearest to image of a lens other than the diffractive optical element DOE, from among the lens surfaces, to be convex toward the image side, the arrangement of optical surfaces becomes a concentric arrangement, which is advantageous for correction of an off-axis aberration such as the astigmatic difference.

Moreover, according to a preferable aspect of each embodiment, it is desirable that the image pickup apparatus satisfies the following conditional expression (4).

$$0.8 < |R_e/R_{img}| < 1.5 \quad (4)$$

where,

Re denotes a radius of curvature of a surface nearest to image out of lens surfaces in the image forming optical system, $R_{img}$ denotes a radius of curvature of a virtual spherical surface including a surface apex and a point at which a principal light ray with the maximum image height of the image forming optical system and the light-receiving surface intersect, when a point of intersection of the optical axis and the light-receiving surface is let to be the surface apex, and when the focal length of the image forming optical system is variable, conditional expression (4) is a conditional expression in a state at a wide angle end.

Conditional expression (4) regulates an appropriate ratio of the radius of curvature of the surface nearest to image out of the lens surfaces and $R_{img}$.

For reducing the astigmatic difference, it is significant to satisfy conditional expression (4).

By making an arrangement such that an upper limit value of conditional expression (4) is not exceeded, it is possible to suppress occurrence of the astigmatic difference.

By making an arrangement such that a value does not fall below a lower limit value of conditional expression (4), the curvature of field is in acceptable range, which is advantageous for small-sizing of the optical system.

It is preferable to satisfy the following conditional expression (4-1) instead of conditional expression (4).

$$0.2 < |R_e/R_{img}| < 1.3 \quad (4\text{-}1)$$

Accordingly, it is possible to show the effect of conditional expression (4) improved further.

Moreover, according to an aspect of each embodiment, it is desirable that the image pickup apparatus satisfies the following conditional expression (5).

$$0.5 < L_{1e}/TL \quad (5)$$

where, $L_{1e}$ denotes an actual distance from a surface nearest to object on the optical axis of the image forming optical system up to a surface different from a cover glass, which is a surface positioned nearest to the light-receiving surface and adjacent to air, in the image forming optical system TL denotes the practical distance on the optical axis of the image forming optical system, from a surface of incidence of the image forming optical system up to the light-receiving surface, and when the focal length of the image forming optical system is variable, conditional expression (5) is a conditional expression in a state at a wide angle end.

Conditional expression (5) regulates an appropriate ratio of $L_{1e}$ and TL.

By satisfying conditional expression (5), since it is possible to make the image pickup apparatus small-sized with a short back focus, it is more preferable.

It is preferable to satisfy the following conditional expression (5-1) instead of conditional expression (5).

$$0.5 < L_{1e}/TL < 0.9 \quad (5\text{-}1)$$

Accordingly, it is possible to show an effect of conditional expression (5) improved further. By making the back focus short by making an arrangement such that a value does not fall below a lower limit value of conditional expression (5-1), it is further advantageous for shortening the overall length of the optical system. By securing the back focus by making an arrangement such that an upper limit value of conditional expression (5-1) is not exceeded, it is advantageous for small-sizing of an optical system portion.

Moreover, according to a preferable aspect of each embodiment, it is desirable that the image pickup apparatus satisfies the following conditional expression (6).

$$0.05 < PS \times f < 0.8 \quad (6)$$

where,

PS denotes Petzval's sum for the image forming optical system, and

Petzval's sum PS is expressed by the following expression.

$$PS = \sum_{i=1}^{k} \frac{1}{n_i \times f_i}$$

here, i denotes an order of lenses from the object side in the image forming optical system, k denotes the total number of lenses in the image forming optical system, $n_i$ denotes a refractive index of an $i^{th}$ lens about a d-line $f_i$ denotes a focal length of the $i^{th}$ lens, f denotes a focal length of the image forming optical system, and when the focal length of the image forming optical system is variable, conditional expression (6) is a conditional expression in a state at the wide angle end.

By satisfying conditional expression (6), it is possible to achieve an image pickup apparatus in which both the correction of the curvature of field and small-sizing have been achieved.

Moreover, according to a preferable aspect of each embodiment, it is desirable that the image pickup apparatus satisfies the following conditional expression (7).

$$-3.0 < PS \times EXP < -0.1 \quad (7)$$

where,

PS denotes Petzval's sum for the image forming optical system, and

Petzval's sum PS is expressed by the following expression.

$$PS = \sum_{i=1}^{k} \frac{1}{n_i \times f_i}$$

here, i denotes an order of lenses from the object side in the image forming optical system, k denotes the total number of lenses in the image forming optical system, $n_i$ denotes a refractive index of an $i^{th}$ lens about a d-line $f_i$ denotes a focal length of the $i^{th}$ lens, f denotes a focal length of the image forming optical system, EXP denotes a distance from the light-receiving surface up to a paraxial exit-pupil position, and is let to have a negative sign when the paraxial exit-pupil position is on the object side of the light-receiving element, and when the focal length of the image forming optical system is variable, conditional expression (7) is a conditional expression in a state at the wide angle end.

By satisfying conditional expression (7), it is possible to achieve an image pickup apparatus of a small-size optical system in which the curvature of field is corrected further, and a position of an exit pupil is near the image plane.

Moreover, it is desirable that the image pickup apparatus further includes an illuminating unit and a cover portion which is disposed on the object side of the image forming optical system.

By disposing the cover portion, it is possible to make an arrangement such that a distance between an object and the image forming optical system is not excessively close, which is advantageous for letting the object in a depth of field. Including the illuminating unit is advantageous for night photography and intracavitary photography.

Furthermore, it is preferable that the cover portion has a dome shape covering an object side of both the image forming optical system and the illuminating unit.

Accordingly, it is possible to make an arrangement such that a distance between the object and the illuminating unit is not excessively close, and to reduce whiteout in an image captured.

Moreover, a capsule endoscope according to another embodiment includes the abovementioned image pickup apparatus, an illuminating unit, and a cover portion having a dome shape disposed on an object side of both the image forming optical system and the illuminating unit.

Since the image pickup apparatus according to each embodiment described above is advantageous for small-sizing, it is preferable to make an arrangement as a capsule endoscope that includes the illuminating unit and the cover portion having a dome shape.

Examples of image pickup apparatuses according to certain aspects of the present invention, and the capsule endoscope will be described below in detail by referring to the accompanying diagrams. However, the present invention is not limited to the examples described below.

Aberration diagrams will be described below. FIG. 2A, FIG. 4A, FIG. 6A, FIG. 8A, FIG. 10A, FIG. 12A, FIG. 13A, FIG. 14A, and FIG. 16A show a spherical aberration (SA), FIG. 2B, FIG. 4B, FIG. 6B, FIG. 8B, FIG. 10B, FIG. 12B, FIG. 13B, FIG. 14B, and FIG. 16B show an astigmatism (AS), FIG. 2C, FIG. 4C, FIG. 6C, FIG. 8C, FIG. 10C, FIG. 12C, FIG. 13C, FIG. 14C, and FIG. 16O show a distortion (DT), and FIG. 2D, FIG. 4D, FIG. 6D, FIG. 8D, FIG. 10D, FIG. 12D, FIG. 13D, FIG. 14D, and FIG. 16D show a transverse aberration in a tangential direction and a sagittal direction. An upper end of a vertical axis in the aberration diagrams of the astigmatism (AS) and the distortion (DT) corresponds to the maximum angle of view. Moreover, the astigmatism (AS) indicates an amount of aberration from a light-receiving surface (an image pickup surface) that is curved.

FIG. 1 shows a lens cross-sectional view of an image pickup apparatus according to an example 1 of the present invention. FIG. 2A, FIG. 2B, FIG. 2C, and FIG. 2D are aberration diagrams of the image pickup apparatus according to the example 1.

The image pickup apparatus according to the present example includes in order from an object side, a planoconvex positive lens L1 having a convex surface directed toward the object side and a planoconvex positive lens L2 having a convex surface directed toward an image side. A light-receiving surface (an image pickup surface) I is a spherical surface and is curved to be concave toward the object side. The planoconvex positive lens L1 and the planoconvex positive lens L2 are cemented.

An aperture stop S is disposed between the planoconvex positive lens L1 and the planoconvex positive lens L2. An aspheric surface is provided to two surfaces namely, an object-side surface of the planoconvex positive lens L1 and an image-side surface of the planoconvex positive lens L2. A diffracting optical surface is provided to an image-side surface of the planoconvex positive lens L2.

Figure 3:
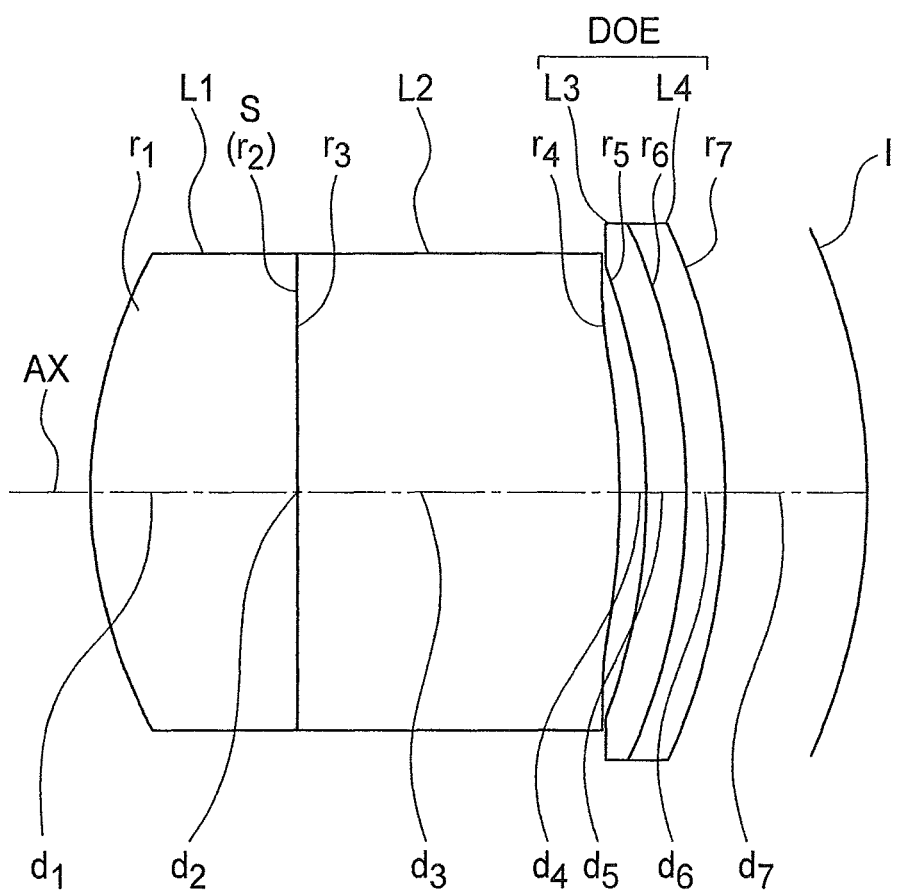
FIG. 3 is a cross-sectional view of an image pickup apparatus according to an example 2 of the present invention.
Figure 4A:
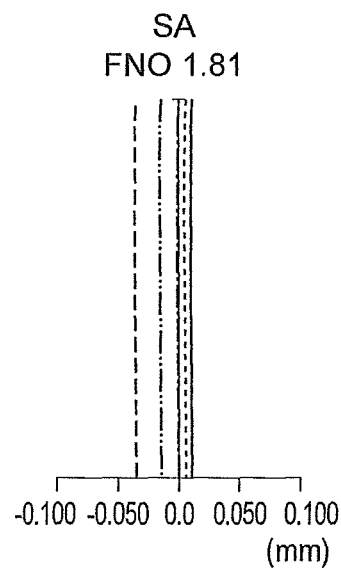
FIG. 4A, FIG. 4B, FIG. 4C, and FIG. 4D are aberration diagrams of the image pickup apparatus according to the example 2.
Figure 4B:
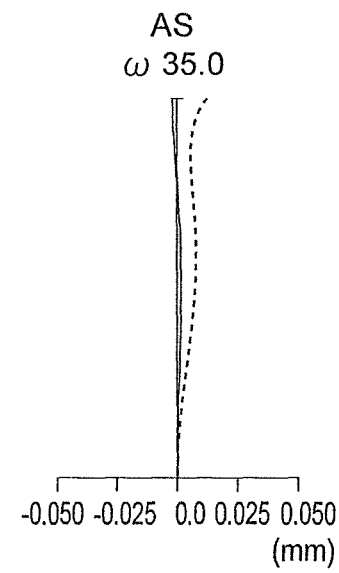
Figure 4C:
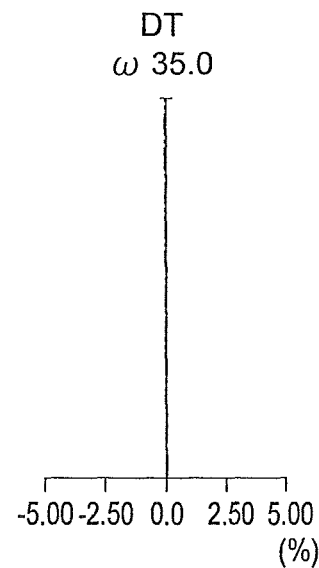
Figure 4D:
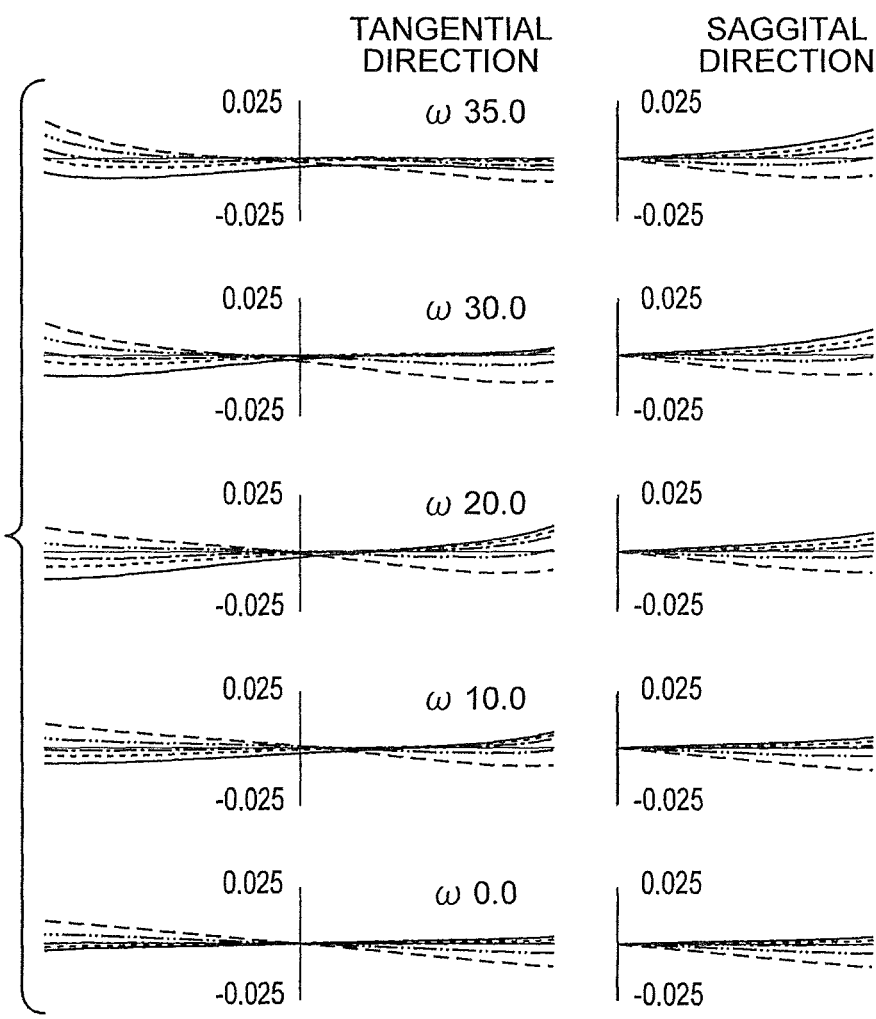

FIG. 3 shows a lens cross-sectional view of an image pickup apparatus according to an example 2 of the present invention. FIG. 4A, FIG. 4B, FIG. 4C, and FIG. 4D are aberration diagrams of the image pickup apparatus according to the example 2.

The image pickup apparatus according to the present example includes in order from an object side, a planoconvex positive lens L1 having a convex surface directed toward the object side, a planoconvex positive lens L2 having a convex surface directed toward an image side, a meniscus lens L3 having a convex surface directed toward the image side, and a meniscus lens L4 having a convex surface directed toward the image side. A light-receiving surface (an image pickup surface) I is a spherical surface, and is curved to be concave toward the object side. The planoconvex positive lens L1 and the planoconvex positive lens L2 are cemented. The meniscus lens L3 and the meniscus lens L4 are cemented.

An aperture stop S is disposed between the planoconvex positive lens L1 and the planoconvex positive lens L2. An aspheric surface is provided to two surfaces namely, an object-side surface of the planoconvex positive lens L1 and an image-side surface of the planoconvex positive lens L2. A diffracting optical surface is provided to an image-side surface of the meniscus lens L3. Moreover, the meniscus lens L3 and the meniscus lens L4 form a diffractive optical element DOE.

Figure 5:
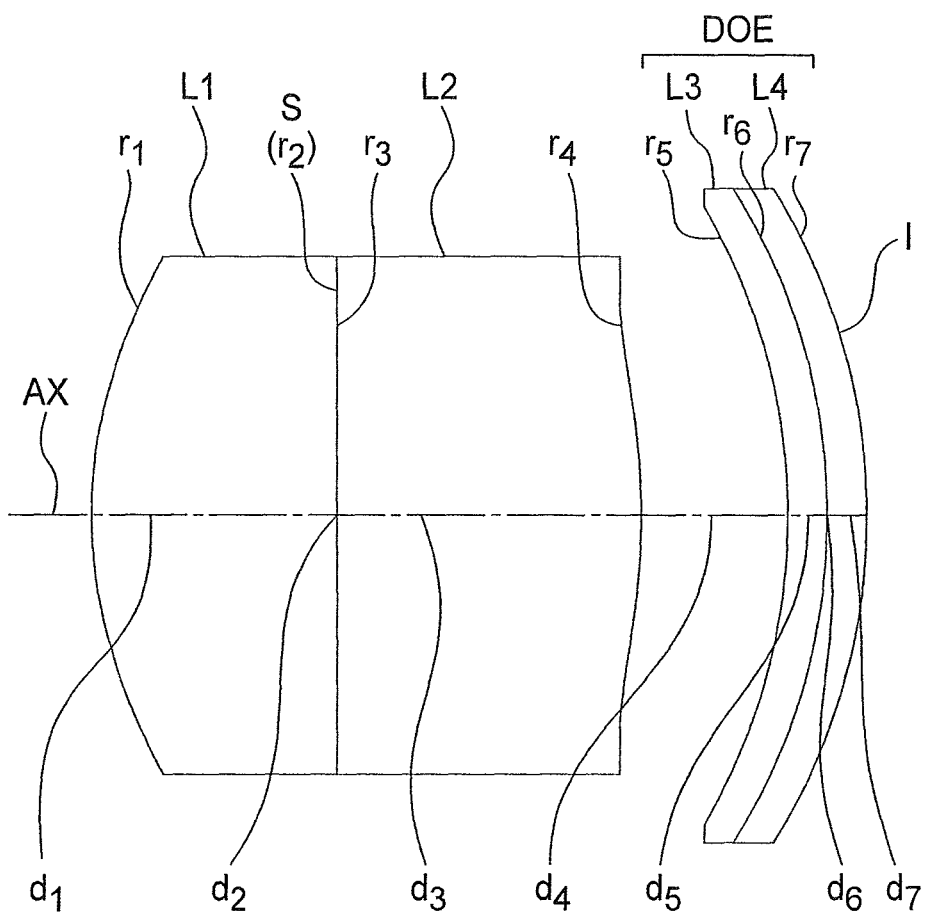
FIG. 5 is a cross-sectional view of an image pickup apparatus according to an example 3 of the present invention.
Figure 8A:
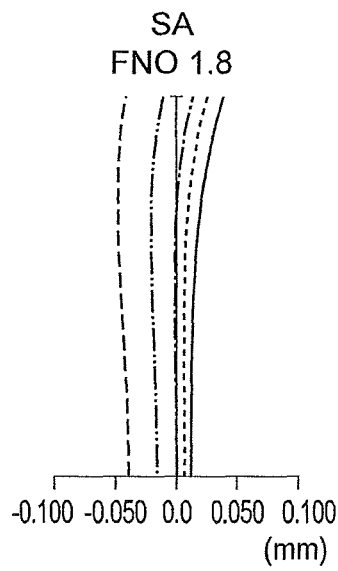
FIG. 8A, FIG. 8B, FIG. 8C, and FIG. 8D are aberration diagrams of the image pickup apparatus according to the example 4.
Figure 8B:
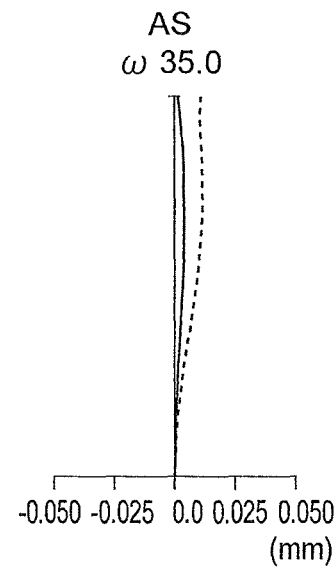
Figure 8C:
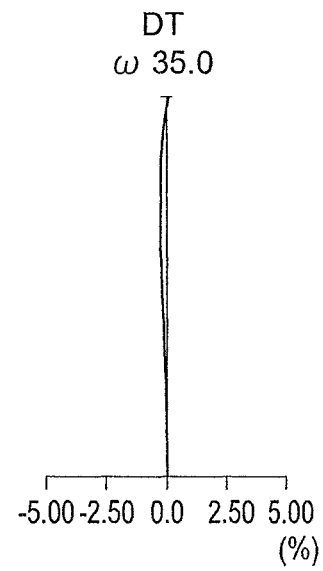
Figure 8D:
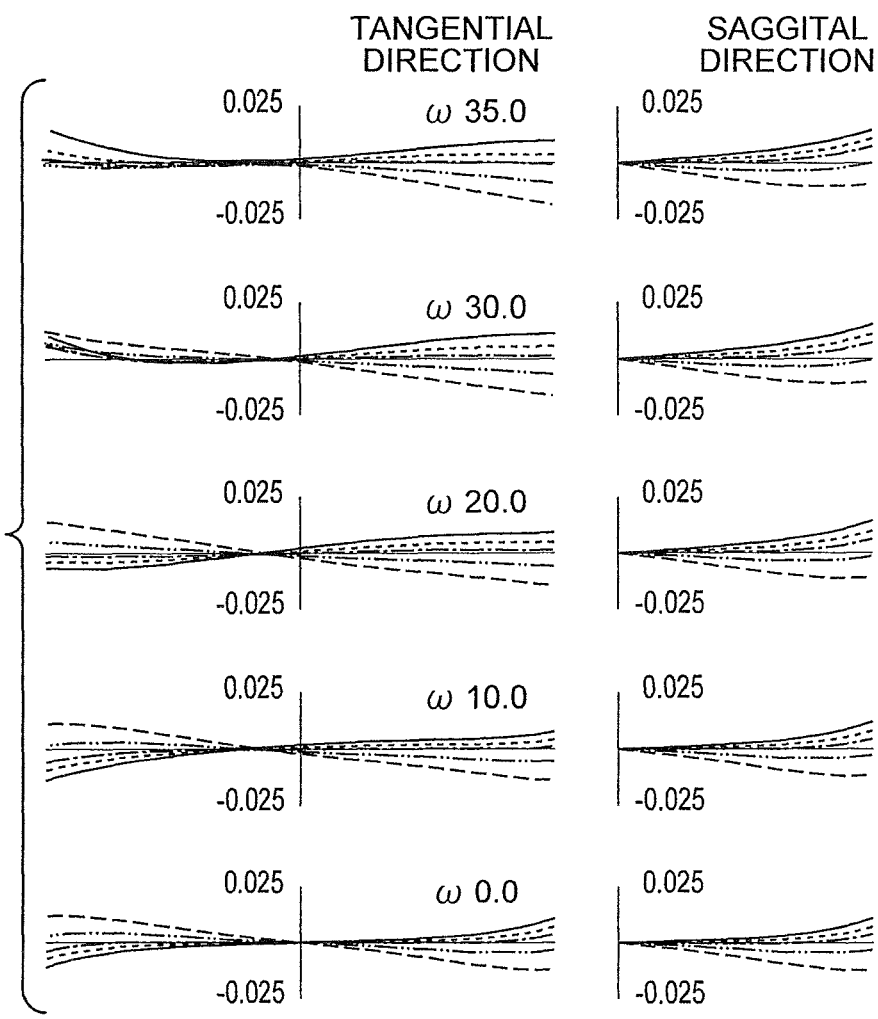

FIG. 5 shows a lens cross-sectional view of an image pickup apparatus according to an example 3 of the present invention. FIG. 6A, FIG. 6B, FIG. 6C, and FIG. 6D are aberration diagrams of the image pickup apparatus according to the example 3.

The image pickup apparatus according to the present example includes in order from an object side, a planoconvex positive lens L1 having a convex surface directed toward the object side, a planoconvex positive lens L2 having a convex surface directed toward an image side, a meniscus lens L3 having a convex surface directed toward the image side, and a meniscus lens L4 having a convex surface directed toward the image side. A light-receiving surface (an image pickup surface) I is a spherical surface, and is curved to be concave toward the object side. The planoconvex positive lens L1 and the planoconvex positive lens L2 are cemented. The meniscus lens L3 and the meniscus lens L4 are cemented.

An aperture stop S is disposed between the planoconvex positive lens L1 and the planoconvex positive lens L2. An aspheric surface is provided to two surfaces namely, an object-side surface of the planoconvex positive lens L1 and an image-side surface of the planoconvex positive lens L2. A diffracting optical surface is provided to an image-side surface of the meniscus lens L3. Moreover, the meniscus lens L3 and the meniscus lens L4 forma diffractive optical element DOE.

In this example, a surface of emergence of the diffractive optical element DOE and the light-receiving surface which is concave are brought into contact, and the diffractive optical element DOE also serves as a cover glass protecting the light-receiving surface of the imager.

FIG. 7 shows a lens cross-sectional view of an image pickup apparatus according to an example 4 of the present invention. FIG. 8A, FIG. 8B, FIG. 8C, and FIG. 8D are aberration diagrams of the image pickup apparatus according to the example 4.

The image pickup apparatus according to the present example includes in order from an object side, a meniscus lens L1 having a convex surface directed toward the object side, a meniscus lens L2 having a convex surface directed toward the object side, a planoconvex positive lens L3 having a convex surface directed toward the object side, and a planoconvex positive lens L4 having a convex surface directed toward an image side. A light-receiving surface (an image pickup surface) I is a spherical surface, and is curved to be concave toward the object side. The meniscus lens L1 and the meniscus lens L2 are cemented. The planoconvex positive lens L3 and the planoconvex positive lens L4 are cemented.

An aperture stop S is disposed between the planoconvex positive lens L3 and the planoconvex positive lens L4. An aspheric surface is provided to two surfaces namely, an object-side surface of the planoconvex positive lens L3 and an image-side surface of the planoconvex positive lens L4. A diffracting optical surface is provided to an image-side surface of the meniscus lens L1. Moreover, the meniscus lens L1 and the meniscus lens L2 form a diffractive optical element DOE.

Figure 9:
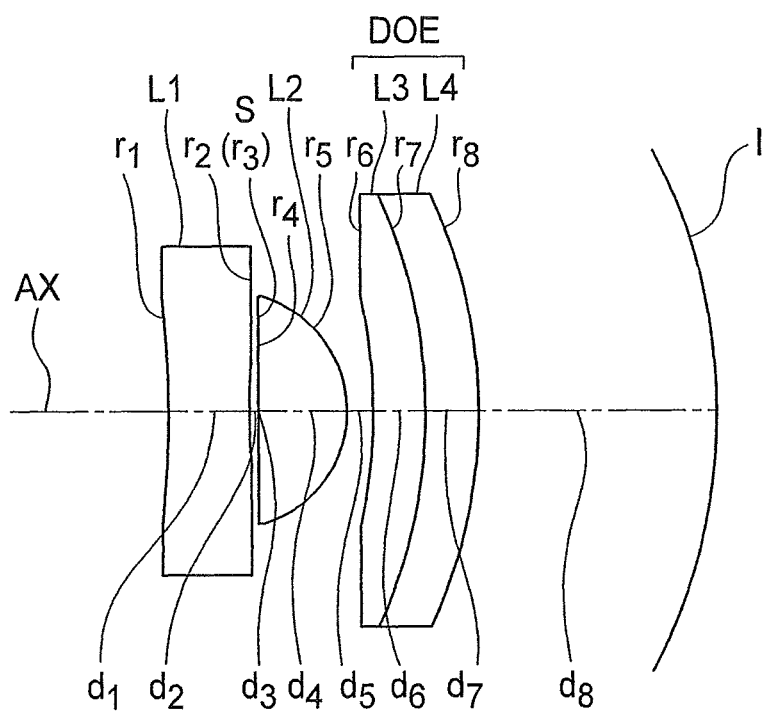
FIG. 9 is a cross-sectional view of an image pickup apparatus according to an example 5 of the present invention.
Figure 10A:
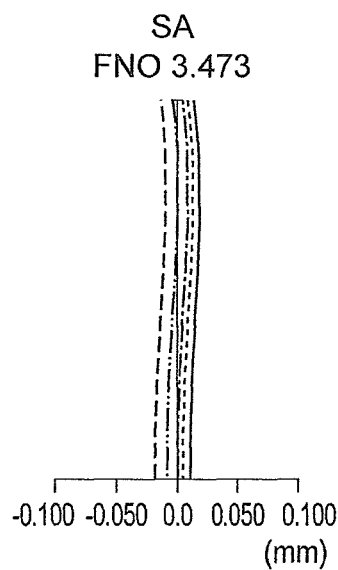
FIG. 10A, FIG. 10B, FIG. 10C, and FIG. 10D are aberration diagrams of the image pickup apparatus according to the example 5.
Figure 10B:
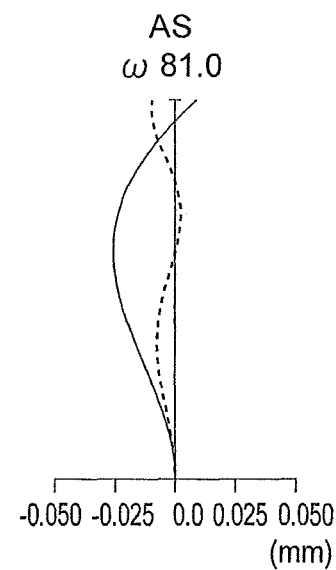
Figure 10C:
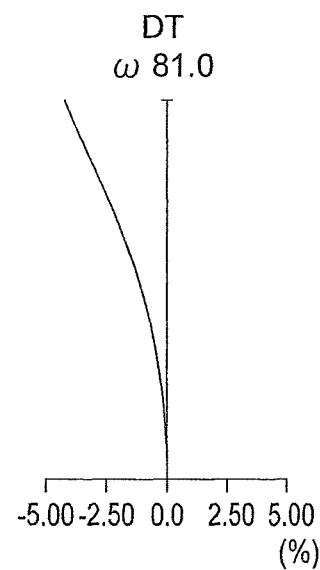
Figure 10D:
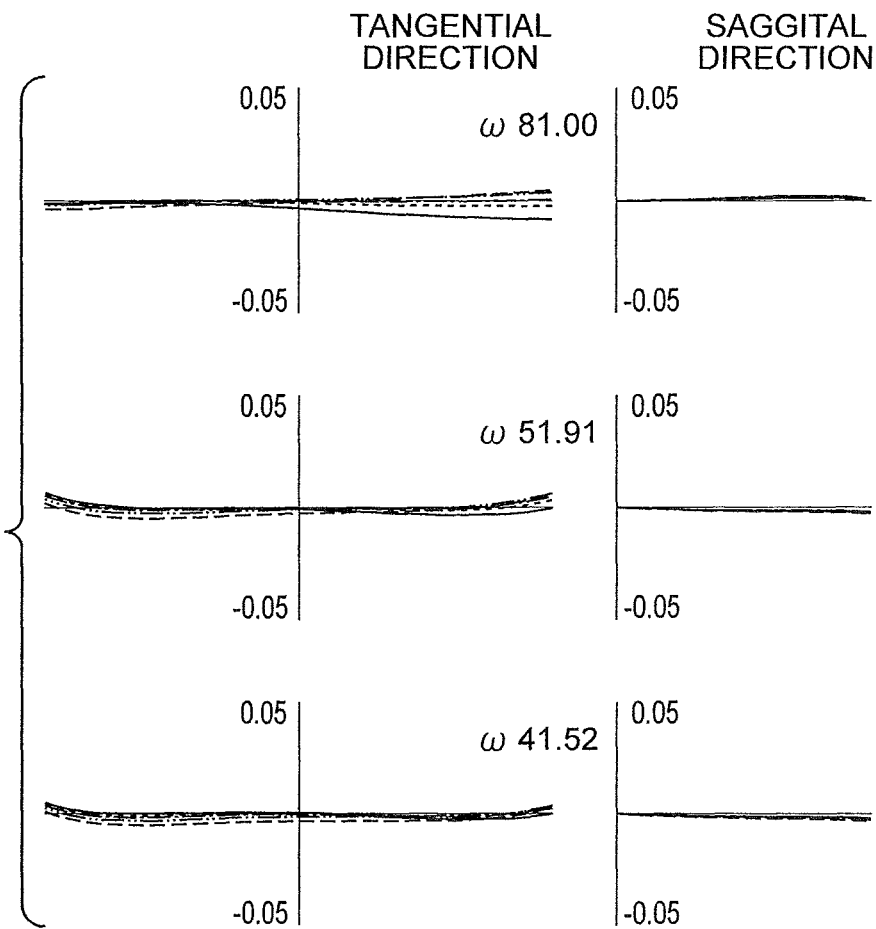

FIG. 9 shows a lens cross-sectional view of an image pickup apparatus according to an example 5 of the present invention. FIG. 10A, FIG. 10B, FIG. 10C, and FIG. 10D are aberration diagrams of the image pickup apparatus according to the example 5.

The image pickup apparatus according to the present example includes in order from an object side, a biconcave negative lens L1, a planoconvex positive lens L2 having a convex surface directed toward an image side, a meniscus lens L3 having a convex surface directed toward the image side, and a meniscus lens L4 having a convex surface directed toward the image side. A light-receiving surface (an image pickup surface) I is a spherical surface, and is curved to be concave toward the object side. The meniscus lens L3 and the meniscus lens L4 are cemented.

An aperture stop S is disposed on an object-side surface of the planoconvex positive lens L2. An aspheric surface is provided to two surfaces namely, both surfaces of the biconcave negative lens L1. A diffracting optical surface is provided to an image-side surface of the meniscus lens L3. Moreover, the meniscus lens L3 and the meniscus lens L4 form a diffractive optical element DOE.

Figure 11A:
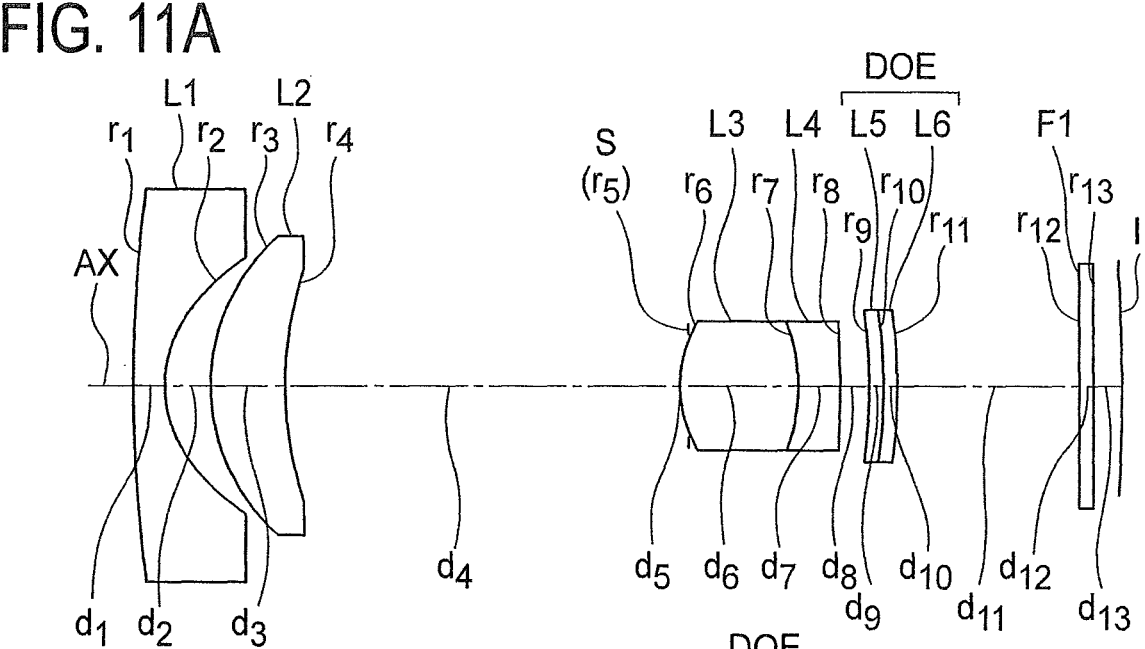
FIG. 11A, FIG. 11B, and FIG. 11C are cross-sectional views of an image pickup apparatus according to an example 6 of the present invention, where.
Figure 11B:
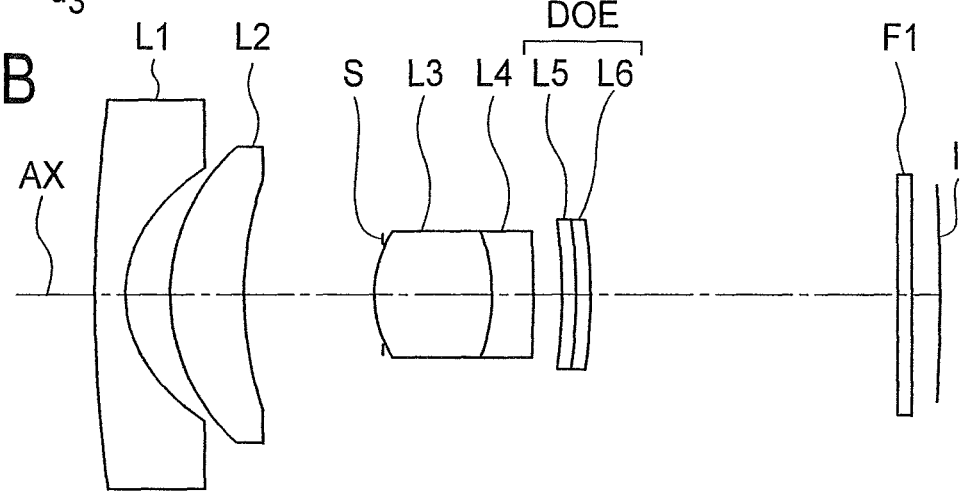
Figure 11C:
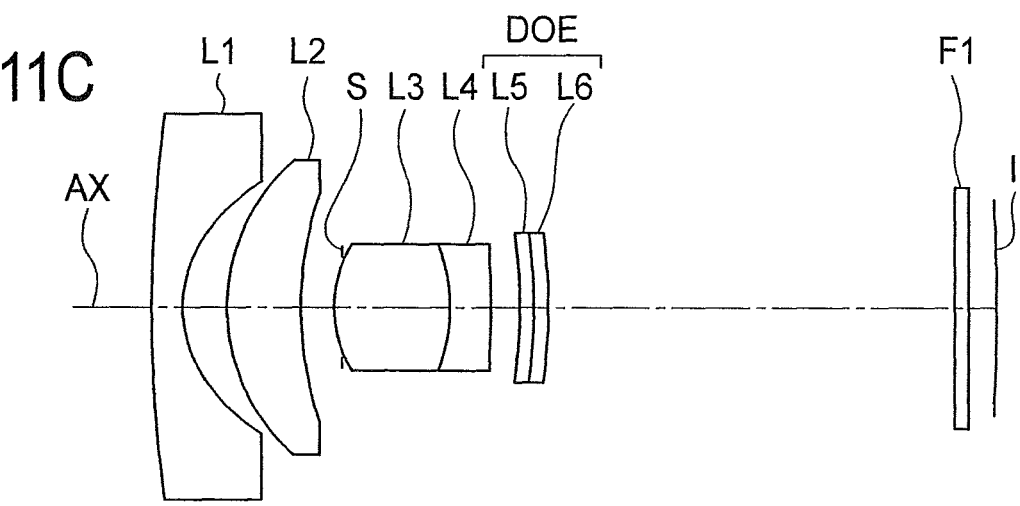
Figure 13A:
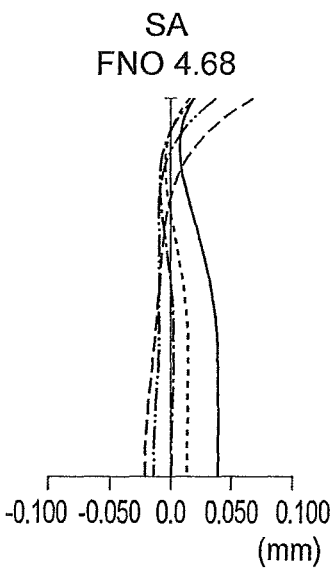
FIG. 13A, FIG. 13B, FIG. 13C, and FIG. 13D are an aberration diagrams in the intermediate focal length state of the image pickup apparatus according to the example 6.
Figure 13B:
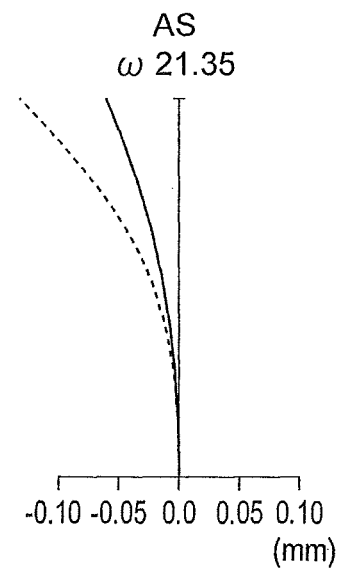
Figure 13C:
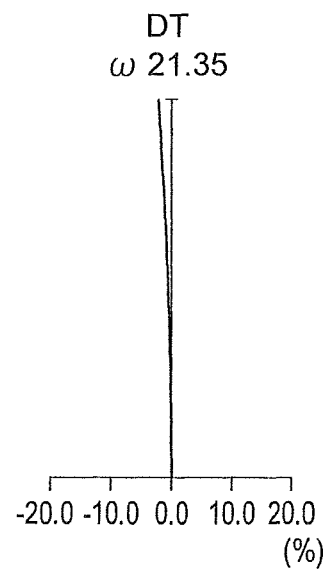
Figure 13D:
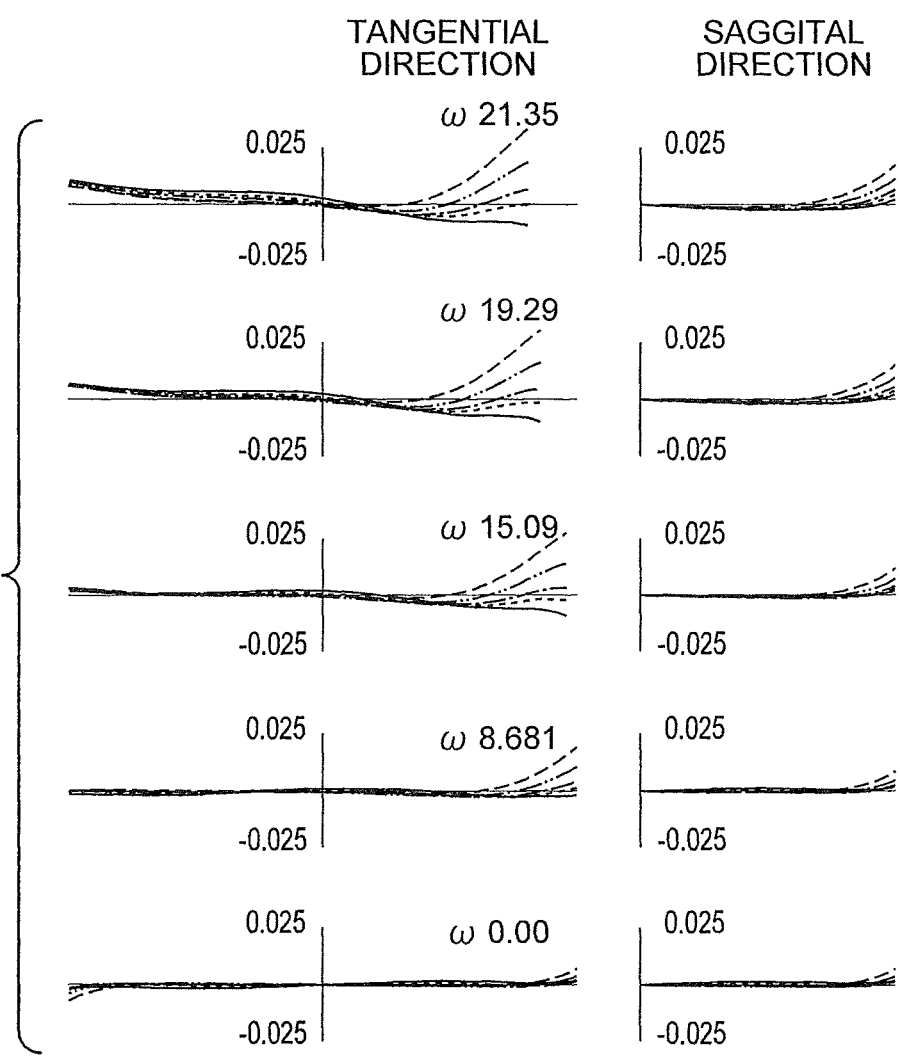

FIG. 11A, FIG. 11B, and FIG. 11C show lens cross-sectional views of an image pickup apparatus according to an example 6 of the present invention. The image pickup apparatus according to the present example has a variable focal length. FIG. 11A, FIG. 11B, and FIG. 11C are lens cross-sectional views in a state at a wide angle end, an intermediate focal length state, and a state at a telephoto end respectively.

The image pickup apparatus according to the present example includes in order from an object side, a negative meniscus lens L1 having a convex surface directed toward the object side, a positive meniscus lens L2 having a convex surface directed toward the object side, a biconvex positive lens L3, a negative meniscus lens L4 having a convex surface directed toward an image side, a meniscus lens L5 having a convex surface directed toward the image side, a meniscus lens L6 having a convex surface directed toward the image side, and a plane-parallel plate F1. A light-receiving surface (an image pickup surface) I is a spherical surface, and is curved to be concave toward the object side. The biconvex positive lens L3 and the negative meniscus lens L4 are cemented. The meniscus lens L5 and the meniscus lens L6 are cemented.

An aperture stop S is disposed between the positive meniscus lens L2 and the biconvex positive lens L3. An aspheric surface is provided to three surfaces namely, an image-side surface of the negative meniscus lens L1, an object-side surface of the biconvex positive lens L3, and an image-side surface of the negative meniscus lens L4. A diffracting optical surface is provided to an image-side surface of the meniscus lens L5. Moreover, the meniscus lens L5 and the meniscus lens L6 form a diffractive optical element DOE.

At the time of zooming from the wide angle end to the telephoto end, the negative meniscus lens L1 and the positive meniscus lens L2, after moving integrally toward the image side move toward the object side, and move integrally only toward the object side from the aperture stop up to the meniscus lens L6.

Focusing is carried out by moving the negative meniscus lens L1 and the positive meniscus lens L2 integrally.

In this embodiment, the image forming optical system is arranged as a two-unit zoom lens. However, the image forming optical system may be arranged as a zoom lens of three or more units. For instance, the plane-parallel plate F1 may be arranged as a negative lens or a positive lens, and the image forming optical system may be formed as a three-unit zoom lens in which the lens units either move or are fixed at the time of zooming.

FIG. 12A, FIG. 12B, FIG. 12C, and FIG. 12D are an aberration diagram in a state at a wide angle end of the present embodiment. FIG. 13A, FIG. 13B, FIG. 13C, and FIG. 13D are an aberration diagram in an intermediate focal length state of the present embodiment. FIG. 14A, FIG. 14B, FIG. 14C, and FIG. 14D are aberration diagrams in a state at a telephoto end of the present embodiment.

Figure 15:
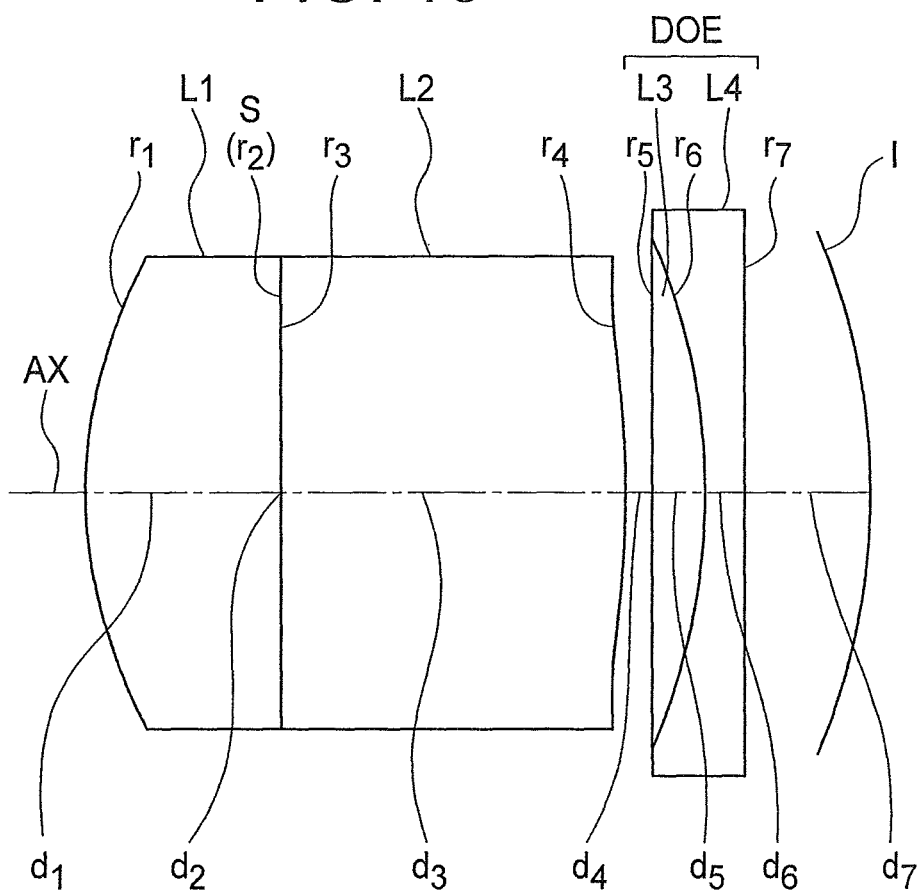
FIG. 15 is a cross-sectional view of an image pickup apparatus according to an example 7 of the present invention.

FIG. 15 shows a lens cross-sectional view of an image pickup apparatus according to an example 7 of the present invention. FIG. 16A, FIG. 16B, FIG. 16C, and FIG. 16D are aberration diagrams of the image pickup apparatus according to the example 7.

The image pickup apparatus according to the present example includes in order from an object side a planoconvex positive lens L1 having a convex surface directed toward the object side, a planoconvex positive lens L2 having a convex surface directed toward an image side, a planoconvex positive lens L3 having a convex surface directed toward the image side, and a planoconcave negative lens L4 having a concave surface directed toward the object side. A light-receiving surface (an image pickup surface) I is an aspheric surface, and is curved to be concave toward the objects side. The planoconvex positive lens L1 and the planoconvex positive lens L2 are cemented. The planoconvex positive lens L3 and the planoconcave negative lens L4 are cemented.

An aperture stop S is disposed between the planoconvex positive lens L1 and the planoconvex positive lens L2. An aspheric surface is provided to two surfaces namely, an object-side surface of the planoconvex positive lens L1 and an image-side surface of the planoconvex positive lens L2. A diffracting optical surface is provided to an image-side surface of the biconvex positive lens L3. Moreover, the planoconvex positive lens L3 and the planoconcave negative lens L4 form a diffractive optical element DOE.

Figure 17A:
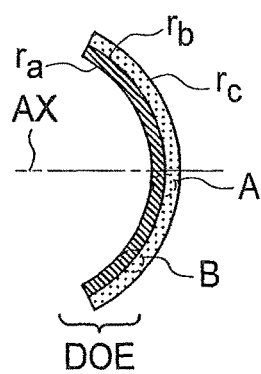
FIG. 17A, FIG. 17B, FIG. 17C, FIG. 17D, FIG. 17E, and FIG. 17F are cross-sectional views of diffractive optical elements.

Next, aspects of a diffractive optical element DOE will be described below. FIG. 17A is a diagram showing an example of a cross-sectional arrangement of a diffractive optical element DOE having a meniscus shape as described in examples 2 to 6. The diffractive optical element DOE includes a meniscus lens having two concentric-circular shaped surfaces ra and rb, and a meniscus lens having two concentric-circular shaped surfaces rb and rc. The diffracting optical surface is formed on the surface rb.

Figure 17B:
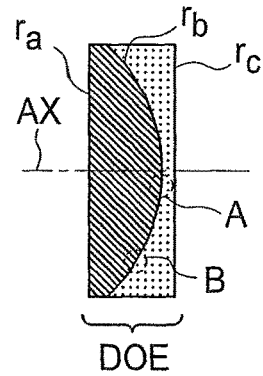

FIG. 17B shows a cross-sectional arrangement of a diffractive optical element DOE in the form of a plane-parallel plate as described in the example 7.

The diffractive optical element DOE includes a planoconvex lens having a flat surface ra and a convex surface rb, and a planoconcave lens having a concave surface rb and a flat surface rc. The diffracting optical surface is formed on the curved surface rb.

A relief pattern of the diffracting optical surface is formed to be rotationally symmetric about an optical axis AX. A pitch of the relief pattern becomes smaller gradually as moving away from the optical axis AX.

Figure 17C:
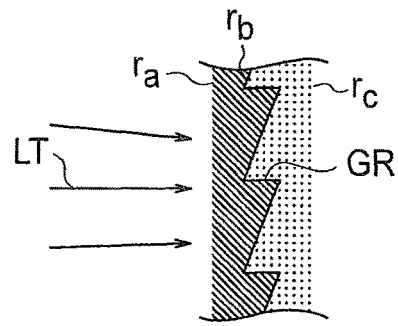

FIG. 17C shows an enlarged cross-sectional arrangement in an area A near the optical axis AX of the diffractive optical element DOE. A cross-sectional shape of the diffracting optical surface, when partially enlarged, has a saw-tooth shape. Moreover, an arrangement has been made such that a principal light ray LT is incident almost parallel to a surface GR of the saw-tooth shape.

Figure 17D:
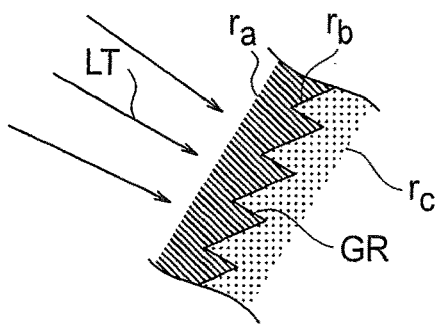

FIG. 17D shows an enlarged cross-sectional arrangement in an off-axis area B of the diffractive optical element DOE. A surface GR is arranged to be inclined with respect to an optical axis AX such that an off-axis principal light ray LT comes closer to being parallel to the surface GR of the saw-tooth shape.

Figure 17E:
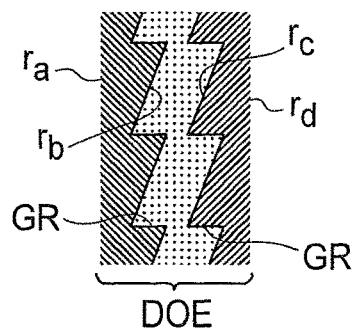
Figure 17F:
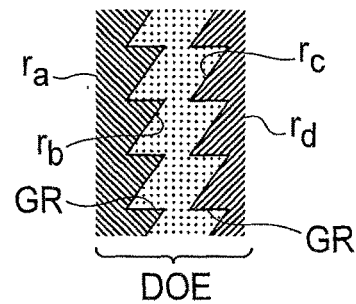

FIG. 17E and FIG. 17F show a cross-sectional arrangement of a diffractive optical element DOE formed of four surfaces ra, rb, rc, and rd. A diffracting optical surface is formed on the surfaces rb and rc.

FIG. 17E is an enlarged view of the area A in FIG. 17A and FIG. 17B. FIG. 17F is an enlarged view of the area B in FIG. 17A and FIG. 17B. Locations corresponding to GR in FIG. 17F (locations corresponding to teeth of saw-tooth shape) are to be arranged to be inclined with respect to the optical axis AX similarly as in FIG. 17D.

Figure 18A:
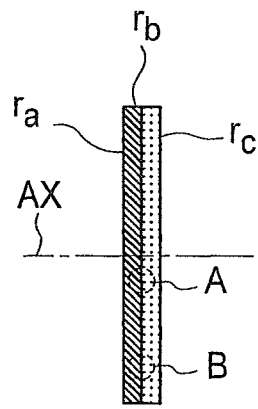
FIG. 18A, FIG. 18B, and FIG. 18C are cross-sectional views of other diffractive optical elements.

FIG. 18A shows a cross-sectional arrangement of a diffractive optical element DOE in the form of a plane-parallel plate. In this example, a flat surface rb is the diffracting optical surface.

Figure 18B:
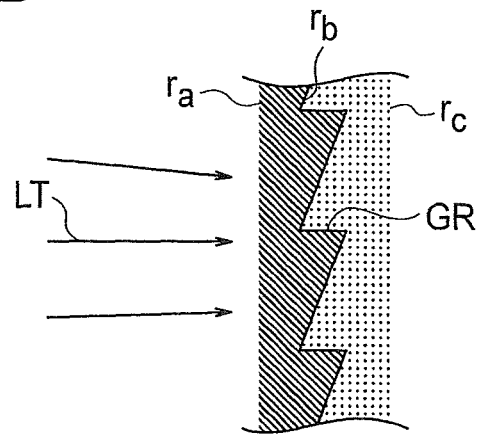

FIG. 18B shows an enlarged cross-sectional arrangement in an area A near an optical axis of a diffractive optical element DOE when a flat surface rb is the diffracting optical surface. The diffracting optical surface has a saw-tooth shape. Moreover, an arrangement is made such that a principal light ray LT is incident almost parallel to a surface GR of the saw-tooth shape.

Figure 18C:
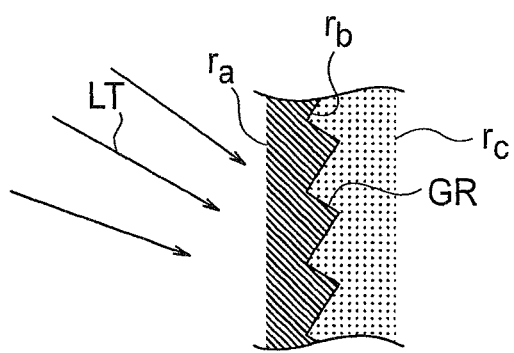

FIG. 18C shows an enlarged cross-sectional arrangement in an off-axis area B of a diffractive optical element DOE when a flat surface rb is the diffracting optical surface. A surface GR is arranged to be inclined with respect to an optical axis AX such that an off-axis principal light ray LT comes closer to being parallel to the surface GR of the saw-tooth shape.

Figure 19:
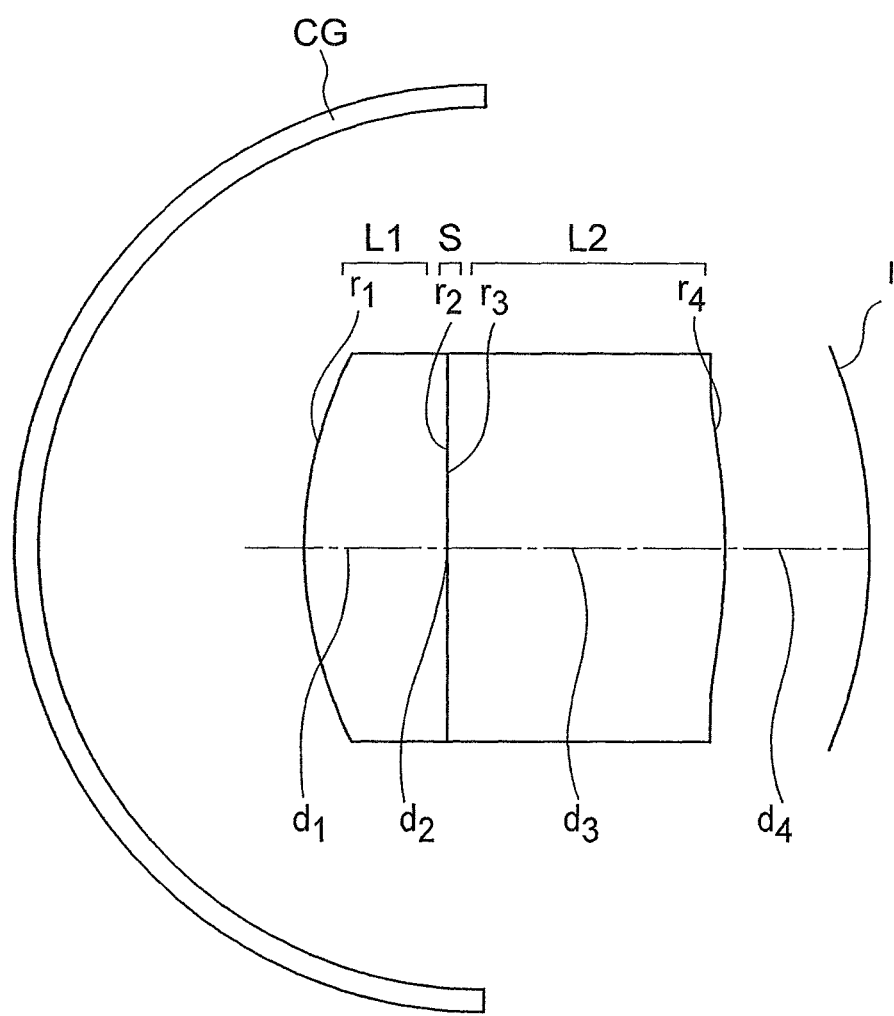
FIG. 19 is a cross-sectional view of an image pickup apparatus according to an example 8 of the present invention.

An image pickup apparatus according to an example 8 of the present invention, as shown in FIG. 19, includes in order from an object side, an optical member CG, a planoconvex positive lens L1 having a convex surface directed toward the object side, and a planoconvex positive lens L2 having a convex surface directed toward an image side. A light-receiving surface (an image pickup surface) I is a spherical surface, and is curved to be concave toward the object side. An optical system including the planoconvex positive lens L1 and the planoconvex positive lens L2 is same as an optical system in the example 1.

FIG. 19 is a schematic diagram exemplifying that the optical member CG can be disposed. Therefore, a size and position of the CG has not been depicted accurately with respect to sizes and positions of lenses.

The optical member CG is a bowl-shaped (dome-shaped) member, and both of an object-side surface and an image-side surface thereof are curved surfaces. In FIG. 19, since both the object-side surface and the image side surface are spherical surfaces having same center of curvature, an overall shape of the optical member is hemispherical. In the present example, a thickness of the optical member CG, or in other words, a distance between the object-side surface and the image side surface is constant in a direction toward the center of curvature.

A material that transmits light is used for the optical member CG. Therefore, light from an object passes through the optical member CG and is incident on the positive lens L1. The optical member CG is disposed such that the center of curvature of the image-side surface substantially coincides with a position of an entrance pupil. Consequently, no new aberration due to the optical member CG occurs practically. In other words, an imaging performance of an image forming optical system in the image pickup apparatus according to the example 8 is same as an imaging performance of an image forming optical system in the image pickup apparatus according to the example 1.

The optical member CG functions as a cover glass. In this case, the optical member CG corresponds to an observation window provided to an outer covering of a capsule endoscope. Therefore, the image pickup apparatus according to the example 8 can be used in an optical system of a capsule endoscope. Image pickup apparatuses according to the examples 2 to 7 can also be used in an optical system of a capsule endoscope.

Numerical data for each of the abovementioned examples is shown below. In surface data, r denotes a radius of curvature of each lens surface, d denotes a distance between two lenses, nd denotes a refractive index about a d-line of each line, vd denotes Abbe's number for each lens, * mark denotes an aspheric surface, and # denotes a diffracting optical surface.

Moreover, in various data, f denotes a focal length of an overall system, FNO denotes an F-number, ω denotes a half angle of view, IH denotes an image height, BF denotes a back focus, and LTL denotes an overall length of an optical system. Here, back focus is a distance from a lens surface nearest to image up to a paraxial image plane indicated upon being subjected to air-conversion. The overall length is a length obtained by adding BF (back focus) to a distance from a lens surface nearest to object up to a lens surface nearest to image of an image forming optical system. Moreover, f1, f2, f3, and f4 denote focal lengths of respective lens units, and the unit of the half angle of view is degrees.

Moreover, when z is let to be an optical axis, y is let to be a direction orthogonal to the optical axis, k is let to be a conical coefficient, and A4, A6, A8, A10, A12, . . . are let to be aspherical-surface coefficients, a shape of the aspheric surface is expressed by the following expression.

$$z=(y^2/r)/[1+\{1-(K+1)(y/r)^2\}^{1/2}]+A4y^4+A6y^6+A8y^8+A10y^{10}+A12y^{12}+\ldots$$

Moreover, 'E-n' (where, n is an integral number) indicates '$10^{-n}$'. Symbols of these original values are same even in the numerical data for the examples that will be described later.

Moreover, when z is let to be an optical axis, y is let to be a direction orthogonal to the optical axis, m is let to be an order of diffraction, r0 is let to be a designed wavelength (nm), and C1, C2, C3, C3, C4, C5, . . . are let to be phrase coefficients, a phase function which indicates diffraction characteristic of a diffractive optical element DOE is expressed by the following expression.

$$\varphi=\{2\pi/(m\times r0)\}\times(C1y^2+C2y^4+C3y^6+C4y^8+C5y^{10}+\ldots)$$

Example 1

| | | Unit mm | | |
|---|---|---|---|---|
| | | Surface data | | |
| Surface no. | r | d | nd | vd |
| Object plane | ∞ | ∞ | | |
| 1* | 3.62689 | 1.502606 | 1.806098 | 40.8817 |
| 2 (Stop) | ∞ | 0.000000 | | |
| 3 | ∞ | 2.877141 | 1.806098 | 40.8817 |
| 4*# | −5.90788 | 1.501005 | | |
| Image plane | −4.92333 | 0.000000 | | |

Aspherical surface data

1st surface

K = −1.000000
A4 = −0.447738E−03, A6 = −0.716882E−04, A8 = 0.000000E+00,
A10 = 0.000000E+00
4th surface K = −1.000000
A4 = −0.533779E−02, A6 = 0.585234E−02, A8 = 0.000000E+00,
A10 = 0.000000E+00

-continued

| Unit mm |
|---|
| Diffraction optical surface data 4th surface | m: 1.000000
r0: 546.07
C1 = −2.1140E−02, C2 = 1.3198E−02, C3 = −5.9616E−03,
C4 = 5.9691E−04

| Various data | |
|---|---|
| f | 3.268 |
| FNO | 1.8 |
| 2ω | 70 |
| IH | 2.00 |
| LTL | 5.88 |
| BF | 1.50 |
| f1 | 4.473 |
| f2 | 5.570 |

Example 2

| | | Unit mm | | |
|---|---|---|---|---|
| | | Surface data | | |
| Surface no. | r | d | nd | vd |
| Object plane | ∞ | ∞ | | |
| 1* | 3.45520 | 1.570553 | 1.806098 | 40.8817 |
| 2 (Stop) | ∞ | 0.000000 | | |
| 3 | ∞ | 2.434836 | 1.806098 | 40.8817 |
| 4* | −5.86641 | 0.200000 | | |
| 5 | −5.00000 | 0.300000 | 1.699860 | 36.4400 |
| 6# | −5.00000 | 0.300000 | 1.640220 | 23.3800 |
| 7 | −5.00000 | 1.075058 | | |
| Image plane | −4.92224 | 0.000000 | | |

Aspherical surface data

1st surface

K = −1.000000
A4 = 0.516950E−03, A6 = −0.227745E−03, A8 = 0.000000E+00,
A10 = 0.000000E+00
4th surface K = −1.000000
A4 = −0.122482E−04, A6 = 0.583318E−02, A8 = 0.000000E+00,
A10 = 0.000000E+00

| Diffraction optical surface data 6th surface |
|---| m: 1.000000
r0: 546.07
C1 = −2.3888E−02, C2 = 9.9295E−03, C3 = −2.9502E−03

| Various data | |
|---|---|
| f | 3.2577 |
| FNO | 1.8131 |
| 2ω | 70 |
| LH | 2.00 |
| LTL | 5.88 |
| BF | 1.08 |
| f1 | 4.26 |
| f2 | 7.24 |
| f3 (DOE) | 18.40 |

Example 3

Unit mm

Surface data

| Surface no. | r | d | nd | vd |
|---|---|---|---|---|
| Object plane | ∞ | ∞ | | |
| 1* | 3.37802 | 1.843941 | 1.806098 | 40.8817 |
| 2 (Stop) | ∞ | 0.000000 | | |
| 3 | ∞ | 2.270975 | 1.806098 | 40.8817 |
| 4* | −4.93625 | 1.095010 | | |
| 5 | −4.52815 | 0.300000 | 1.699860 | 36.4400 |
| 6# | −4.52815 | 0.300000 | 1.640220 | 23.3800 |
| 7 | −4.52815 | 0.001443 | | |
| Image plane | −4.52815 | 0.000000 | | |

Aspherical surface data

1st surface

K = −1.000000
A4 = 0.176604E−03, A6 = −0.334722E−03, A8 = 0.000000E+00, A10 = 0.000000E+00

4th surface

K = −1.000000
A4 = 0.855081E−02, A6 = 0.255438E−02, A8 = 0.000000E+00, A10 = 0.000000E+00

Diffraction optical surface data
6th surface m: 1.000000
r0: 546.07
C1 = −1.3440E−01, C2 = 4.6438E−02, C3 = −6.6235E−03

Various data

| | |
|---|---|
| f | 3.1862 |
| FNO | 1.8111 |
| 2ω | 70 |
| IH | 2.00 |
| LTL | 5.81 |
| BF | 0.00 |
| f1 | 4.17 |
| f2 | 6.09 |
| f3 (DOE) | 3.61 |

Example 4

Unit mm

Surface data

| Surface no. | r | d | nd | vd |
|---|---|---|---|---|
| Object plane | ∞ | ∞ | | |
| 1 | 5.00000 | 0.300000 | 1.640220 | 23.3800 |
| 2# | 5.00000 | 0.300000 | 1.699860 | 36.4400 |
| 3 | 5.00000 | 0.300000 | | |
| 4* | 4.35362 | 2.213781 | 1.806098 | 40.8817 |
| 5 (Stop) | ∞ | 0.000000 | | |
| 6 | ∞ | 1.672909 | 1.806098 | 40.8817 |
| 7* | −4.17000 | 1.814420 | | |
| Image plane | −4.72633 | 0.000000 | | |

Diffraction optical surface data
2nd surface m: −1.000000
r0: 546.07
C1 = 4.2001E−03, C2 = −2.1479E−03, C3 = 4.6607E−04

Aspherical surface data

4th surface

K = −1.000000
A4 = 0.787316E−03, A6 = −0.194409E−02, A8 = 0.000000E+00, A10 = 0.000000E+00

7th surface

K = −1.000000
A4 = 0.325146E−02, A6 = 0.618141E−03, A8 = 0.000000E+00, A10 = 0.000000E+00

Various data

| | |
|---|---|
| f | 3.3873 |
| FNO | 1.8041 |
| 2ω | 70 |
| IH | 2.00 |
| LTL | 6.60 |
| BF | 1.81 |
| f1 (DOE) | 66.94 |
| f2 | 5.37 |
| f3 | 5.143 |

Example 5

Unit mm

Surface data

| Surface no. | r | d | nd | vd |
|---|---|---|---|---|
| Object plane | ∞ | 10.000000 | | |
| 1* | −3.93249 | 0.307754 | 1.531100 | 56.0000 |
| 2* | 7.67122 | 0.034922 | | |
| 3 (Stop) | ∞ | 0.000000 | | |
| 4 | ∞ | 0.336921 | 1.531100 | 56.0000 |
| 5 | −0.45458 | 0.100000 | | |
| 6 | −2.00000 | 0.200000 | 1.699860 | 36.4400 |
| 7# | −2.00000 | 0.200000 | 1.640220 | 23.3800 |
| 8 | −2.00000 | 0.902739 | | |
| Image plane | −2.16926 | 0.000000 | | |

Aspherical surface data

1st surface

K = 0.000000
A4 = −0.383048E+00, A6 = 0.371317E+01, A8 = −0.835477E+01, A10 = 0.000000E+00

2nd surface

K = 0.000000
A4 = 0.337881E+01, A6 = 0.000000E+00, A8 = 0.000000E+00, A10 = 0.000000E+00

Diffraction optical surface data
7th surface m: 1.000000
r0: 546.07
C2 = −1.8037E−01, C3 = 8.1013E−02

Various data

| | |
|---|---|
| f | 0.999 |
| FNO | 3.4734 |
| 2ω | 162 |
| IH | 0.98 |
| LTL | 2.08 |
| BF | 0.90 |
| f1 | −4.83 |

-continued

Unit mm

| | |
|---|---|
| f2 | 0.85 |
| f3 (DOE) | 36.76 |

Unit mm

Surface data

| Surface no. | r | d | nd | vd |
|---|---|---|---|---|
| Object plane | ∞ | ∞ | | |
| 1 | 50.68527 | 1.100000 | 1.806098 | 40.8817 |
| 2* | 4.27249 | 1.584921 | | |
| 3 | 7.04632 | 2.588126 | 2.0006 | 25.458 |
| 4 | 12.51407 | Variable | | |
| 5 (Stop) | ∞ | −0.300000 | | |
| 6* | 4.28590 | 4.150000 | 1.496999 | 81.5459 |
| 7 | −6.44990 | 1.468289 | 1.688931 | 31.0778 |
| 8* | −21.29464 | 1.000000 | | |
| 9 | −20.00000 | 0.500000 | 1.699860 | 36.4400 |
| 10# | −20.00000 | 0.500000 | 1.640220 | 23.3800 |
| 11 | −20.00000 | Variable | | |
| 12 | ∞ | 0.500000 | 1.516330 | 64.1420 |
| 13 | ∞ | 1.000000 | | |
| Image plane | −70.00000 | 0.000000 | | |

Aspherical surface data

2nd surface

K = −1.377980
A4 = 0.144019E−02, A6 = 0.281264E−05, A8 = 0.291555E−06,
A10 = −0.846747E−08

6th surface

K = −1.858736
A4 = 0.253354E−02, A6 = 0.323612E−04, A8 = 0.113237E−06,
A10 = 0.000000E+00

8th surface

K = 0.000000
A4 = 0.211282E−02, A6 = 0.975950E−04, A8 = 0.354338E−04,
A10 = −0.356804E−05

Diffraction optical surface data
10th surface m: 1.000000
r0: 587.56
C2 = −2.3859E−05, C3 = −3.5769E−05, C4 = 1.0701E−06

Zoom data

| | WE | ST | TE |
|---|---|---|---|
| f | 5.00 | 10.00 | 14.80 |
| FNO | 3.56 | 4.68 | 5.76 |
| 2ω | 82.6738 | 42.7 | 29.092 |
| d4 | 14.235689 | 4.618433 | 1.499323 |
| d11 | 6.448805 | 10.510303 | 14.409341 |
| IH | 3.80 | 3.80 | 3.80 |
| LTL | 34.78 | 29.22 | 30.00 |
| BF | 7.95 | 12.01 | 15.91 |
| f1 | −5.82 | −5.82 | −5.82 |
| f2 | 12.90 | 12.90 | 12.90 |
| f3 | 8.69 | 8.69 | 8.69 |
| f4 (DOE) | 1468.30 | 1468.30 | 1468.30 | f3 is a focal length of the cemented lenses L3 and L4.

Example 7

Unit mm

Surface data

| Surface no. | r | d | nd | vd |
|---|---|---|---|---|
| Object plane | ∞ | ∞ | | |
| 1* | 3.48391 | 1.492111 | 1.806098 | 40.8817 |
| 2 (Stop) | ∞ | 0.000000 | | |
| 3 | ∞ | 2.614811 | 1.806098 | 40.8817 |
| 4* | −7.30110 | 0.200000 | | |
| 5 | ∞ | 0.400000 | 1.699860 | 36.4400 |
| 6# | −5.00000 | 0.300000 | 1.640220 | 23.3800 |
| 7 | ∞ | 0.956499 | | |
| Image plane | −5.15772 | 0.000000 | | |

Aspherical surface data

1st surface

K = −1.000000
A4 = 0.486828E−03, A6 = −0.241644E−03, A8 = 0.000000E+00,
A10 = 0.000000E+00

4th surface

K = −1.000000
A4 = 0.170345E−03, A6 = 0.468599E−02, A8 = 0.000000E+00,
A10 = 0.000000E+00

Diffraction optical surface data
6th surface m: 1.000000
r0: 546.07
C1 = −2.3888E−02, C2 = 9.9295E−03, C3 = −2.4625E−03

Various data

| | |
|---|---|
| f | 3.27 |
| FNO | 1.84 |
| 2ω | 70 |
| IH | 2.00 |
| LTL | 5.96 |
| BF | 0.96 |
| f1 | 4.30 |
| f2 | 9.01 |
| f3 (DOE) | 16.86 |

Values of the conditional expressions of each of the examples are shown below.
(1) |DSD/TL|
(2) |f/Rdoe|
(3) |Sin $\theta_{doe}$ − Sin $\theta_{img}$|
(4) |$R_e/R_{img}$|
(5) $L_{1e}$/TL
(6) PS×f
(7) PS×EXP

| | Example 1 | Example 2 | Example 3 | Example 4 |
|---|---|---|---|---|
| (1) | 0.49 | 0.50 | 0.63 | 0.43 |
| (2) | 0.55 | 0.65 | 0.70 | 0.68 |
| (3) | 0.02 | 0.01 | 0.00 | 0.01 |
| (4) | 1.20 | 1.19 | 1.09 | 0.88 |
| (5) | 0.74 | 0.82 | 0.71 | 0.73 |
| (6) | 0.51 | 0.61 | 0.39 | 0.70 |
| (7) | −0.58 | −0.71 | −2.33 | −0.61 |

| | Example 5 | Example 6 | Example 7 |
|---|---|---|---|
| (1) | 0.31 | 0.20 | 0.54 |
| (2) | 0.50 | 0.25 | 0.65 |
| (3) | 0.02 | 0.00 | 0.01 |

-continued

| | | | |
|---|---|---|---|
| (4) | 0.21 | 0.31 | 1.42 |
| (5) | 0.57 | 0.77 | 0.84 |
| (6) | 0.63 | 0.10 | 0.58 |
| (7) | −0.46 | −0.24 | −0.47 |

Figure 20:
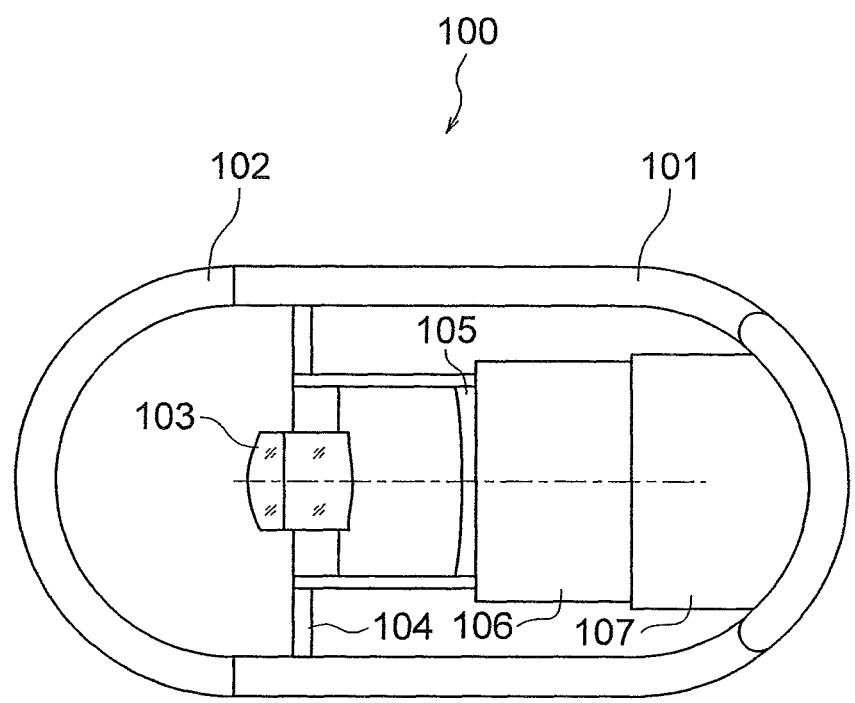
FIG. 20 is a diagram showing a schematic arrangement of a capsule endoscope.

FIG. 20 illustrates an example of a capsule endoscope. In this example, the image pickup apparatus is a capsule endoscope. A capsule endoscope 100 includes a capsule cover 101 and a transparent cover 102. An outer covering of the capsule endoscope 100 is formed by the capsule cover 101 and the transparent cover 102.

The capsule cover 101 includes a central portion having a substantially circular cylindrical shape, and a bottom portion having a substantially bowl shape. The transparent cover 102 is disposed at a position facing the bottom portion, across the central portion. The transparent cover 102 is formed by a transparent member having a substantially bowl shape. The capsule cover 101 and the transparent cover 102 are connected consecutively to be mutually watertight.

An interior of the capsule endoscope 100 includes an image forming optical system 103, a illumination unit 104, an image pickup element 105, a drive control unit 106, and a signal processing unit 107. Although it is not shown in the diagram, the interior of the capsule endoscope 100 is provided with an electric-power receiving unit and a transmitting unit.

Illumination light is irradiated from the illumination unit 104. The illumination light passes through the transparent cover 102 and is irradiated to an object. Light from the object is incident on the image forming optical system 103. An optical image of the object is formed at an image position by the image forming optical system 103.

The optical image is picked up by the image pickup element 105. A drive and control of the image pickup element 105 is carried out by the drive control unit 106. Moreover, an output signal from the image pickup element 105 is processed by the signal processing unit 107 according to the requirement.

Here, for the image forming optical system 103, an optical system which includes the image pickup apparatus according to the abovementioned example 1 has been used. Therefore, an optical image with a favorable optical performance is formed. Moreover, the optical image is curved to be concave toward the object side.

A light-receiving surface (an image pickup surface) of the image pickup element 105 is curved to be concave toward the object side. Moreover, a radius of curvature of the light-receiving surface (image pickup surface) is same as a radius of curvature of the optical image. Consequently, it is possible to achieve an image which is sharp from a center up to periphery, while being an image captured with a favorable optical performance.

Figure 21A:
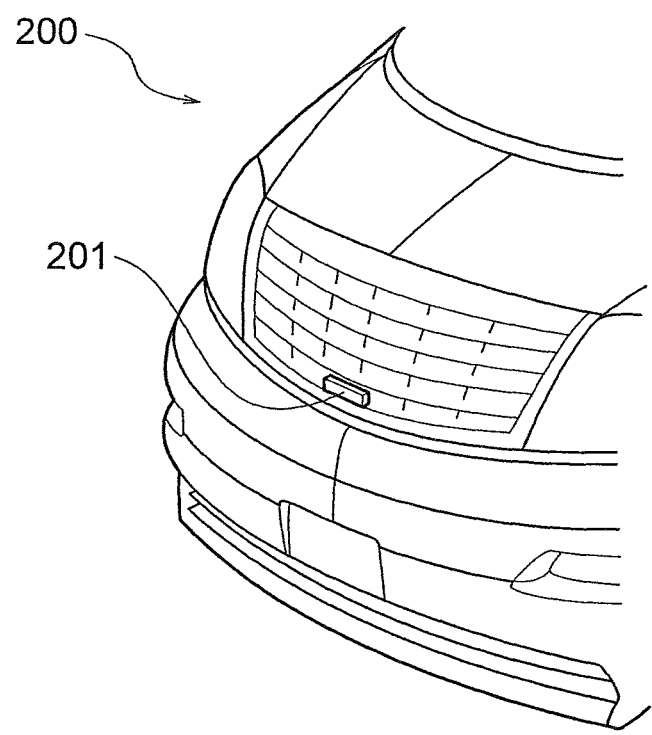
FIG. 21A and FIG. 21B are diagrams showing a car-mounted camera, where.
Figure 21B:
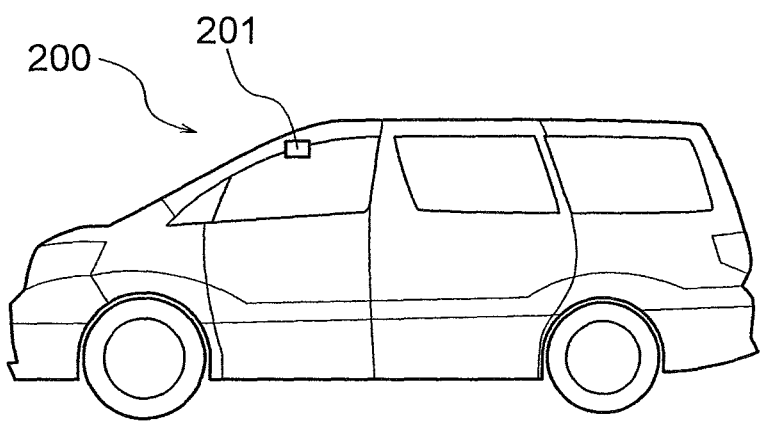

FIG. 21A and FIG. 21B are examples of another image pickup apparatus. This is an example of a car-mounted camera. FIG. 21A is a diagram showing an example of a car-mounted camera mounted at an outside of a car, and FIG. 21B is a diagram showing an example of a car-mounted camera mounted inside the car.

As shown in FIG. 21A, a car-mounted camera 201 is provided to a front grill of a car 200. The car-mounted camera 201 includes an image forming optical system and an image pickup element.

For the image forming optical system of the car-mounted camera 201, the optical system that includes the image pickup apparatus according to the abovementioned example 1 is used. Therefore, an optical image of an extremely wide range is formed. Moreover, a light-receiving surface (an image pickup surface) of the image pickup element is curved to be concave toward the object side. Furthermore, a radius of curvature of the light-receiving surface (image pickup surface) is same as a radius of curvature of the optical image. Consequently, it is possible to achieve an image which is sharp from a center up to a periphery, while being an image captured over an extremely wide range.

As shown in FIG. 21B, the car-mounted camera 201 is provided near a ceiling of the car 200. An action and effect of the car-mounted camera 201 is as already described.

The car-mounted camera 201, when to be provided outside, may be disposed at each corner and at the top of a pole of a head portion. Moreover, the car-mounted camera 201, when to be provided inside, may be provided near a back mirror.

Moreover, it is preferable to satisfy the plurality of abovementioned inventions simultaneously as each of the effects of small-sizing, high performance, and widening of angle of view is more assured.

Various embodiments of the present invention have been described heretofore. However, the present invention is not limited only to these embodiments, and embodiments in which arrangements of these embodiments have been combined appropriately without departing from the scope of the invention are also within the scope of the present invention.

As heretofore described, the present invention is useful for an image pickup apparatus and a capsule endoscope including an image forming optical system which is advantageous for correction of the chromatic aberration as well, and enables to achieve a favorable optical performance, and in which there is no need to make Petzval's sum of the optical system small, and it is easy to carry out reduction in the number of lenses and small-sizing The present invention shows an effect that it is possible to provide an image pickup apparatus and a capsule endoscope including an image forming optical system which is advantageous for correction of the chromatic aberration as well, and enables to achieve a favorable optical performance, and in which, there is no need to make Petzval's sum of the optical system small, and it is easy to carry out reduction in number of lenses and small-sizing.

What is claimed is:
1. An image pickup apparatus, comprising:
an image forming optical system which includes:
  an aperture stop that sets an axial light beam; and
  a diffracting optical surface disposed at a position different from a position where the aperture stop is disposed, the diffracting optical surface having a relief pattern formed to be rotationally symmetric about an optical axis of the image forming optical system; and
an imager disposed on an image side of the image forming optical system, the imager having a light-receiving surface which is curved to be concave toward the image forming optical system, and the imager outputting an image signal based on light received on the light-receiving surface,
wherein:
the diffracting optical surface satisfies the following conditional expression (1)

$$0.1 < |DSD/TL| \leq 1.0 \quad (1)$$

where,
TL denotes an actual distance on the optical axis of the image forming optical system, from a surface of incidence of the image forming optical system up to the light-receiving surface,
DSD denotes an actual distance on the optical axis of the image forming optical system, from a position of the aperture stop up to the diffracting optical surface, and
when a focal length of the image forming optical system is variable, conditional expression (1) is a conditional expression in a state at a wide angle end.

2. The image pickup apparatus according to claim 1, wherein:
the diffracting optical surface is disposed at any position on a lens surface nearest to an image of the image forming optical system up to the light-receiving surface, and
the image pickup apparatus satisfies the following conditional expression (3)

$$0.0 \le |\sin \theta_{doe} - \sin \theta_{img}| < 0.1 \qquad (3)$$

where,
$\theta_{doe}$ denotes an angle with respect to the optical axis of a virtual line connecting a point at which a principal light ray with a maximum image height of the image forming optical system and the diffracting optical surface intersect, and a center of curvature of the diffracting optical surface,
$\theta_{img}$ denotes an angle with respect to the optical axis of a virtual line connecting a point at which the principal light ray with the maximum image height of the image forming optical system and the light-receiving surface intersect, and a center of curvature of the light-receiving surface, and
when the focal length of the image forming optical system is variable, conditional expression (3) is a conditional expression in a state at the wide angle end.

3. The image pickup apparatus according to claim 1, wherein the image forming optical system includes at least one aspheric surface.

4. The image pickup apparatus according to claim 1, wherein out of lens surfaces in the image forming optical system, a surface nearest to an image is a surface which is convex toward the image side.

5. The image pickup apparatus according to claim 1, wherein the image pickup apparatus satisfies the following conditional expression (4)

$$0.8 < |R_e/R_{img}| < 1.5 \qquad (4)$$

where,
Re denotes a radius of curvature of a surface nearest to an image out of lens surfaces in the image forming optical system,
$R_{img}$ denotes a radius of curvature of a virtual spherical surface including a surface apex and a point at which a principal light ray with a maximum image height of the image forming optical system and the light-receiving surface intersect, when a point of intersection of the optical axis and the light-receiving surface is let to be the surface apex, and
when the focal length of the image forming optical system is variable, conditional expression (4) is a conditional expression in a state at a wide angle end.

6. The image pickup apparatus according to claim 1, wherein the image pickup apparatus satisfies the following conditional expression (5)

$$0.5 < L_{1e}/TL \qquad (5)$$

where,
$L_{1e}$ denotes an actual distance from a surface nearest to an object on the optical axis of the image forming optical system up to a surface different from a cover glass, which is a surface positioned nearest to the light-receiving surface and adjacent to air, in the image forming optical system,
TL denotes a practical distance on the optical axis of the image forming optical system, from a surface of incidence of the image forming optical system up to the light-receiving surface, and
when the focal length of the image forming optical system is variable, conditional expression (5) is a conditional expression in a state at a wide angle end.

7. The image pickup apparatus according to claim 1, wherein the image pickup apparatus satisfied the following conditional expression (6)

$$0.05 < PS \times f < 0.8 \qquad (6)$$

where,
PS denotes Petzval's sum for the image forming optical system, and
Petzval's sum PS is expressed by the following expression $$PS = \sum_{i=1}^{k} \frac{1}{n_i \times f_i}$$

here,
i denotes an order of lenses from an object side in the image forming optical system,
k denotes a total number of the lenses in the image forming optical system,
$n_i$ denotes a refractive index of an $i^{th}$ lens about a d-line,
$f_i$ denotes a focal length of the $i^{th}$ lens,
f denotes a focal length of the image forming optical system, and
when the focal length of the image forming optical system is variable, conditional expression (6) is a conditional expression in a state at the wide angle end.

8. The image pickup apparatus according to claim 1, wherein the image pickup apparatus satisfies the following conditional expression (7)

$$-3.0 < PS \times EXP < -0.1 \qquad (7)$$

where,
PS denotes Petzval's sum for the image forming optical system, and
Petzval's sum PS is expressed by the following expression $$PS = \sum_{i=1}^{k} \frac{1}{n_i \times f_i}$$

here,
i denotes an order of lenses from an object side in the image forming optical system,
k denotes a total number of the lenses in the image forming optical system,
$n_i$ denotes a refractive index of an $i^{th}$ lens about a d-line,
$f_i$ denotes a focal length of the $i^{th}$ lens,
f denotes a focal length of the image forming optical system, EXP denotes a distance from the light-receiving surface up to a paraxial exit-pupil position, and is let to have a negative sign when the paraxial exit-pupil position is on an object side of the light-receiving element, and when the focal length of the image forming optical system is variable, conditional expression (7) is a conditional expression in a state at the wide angle end.

9. The image pickup apparatus according to claim 1, further comprising:
a light source; and
a cover portion which is disposed on an object side of the image forming optical system.

10. The image pickup apparatus according to claim 9, wherein the cover portion has a dome shape covering an object side of both the image forming optical system and the light source.

11. A capsule endoscope, comprising
an image pickup apparatus according to claim 1;
a light source; and
a cover portion having a dome shape disposed on an object side of both the image forming optical system and the light source.

12. An image pickup apparatus, comprising:
an image forming optical system which includes:
an aperture stop that sets an axial light beam, and
a diffracting optical surface disposed at a position different from a position where the aperture stop is disposed, the diffracting optical surface having a relief pattern formed to be rotationally symmetric about an optical axis of the image forming optical system; and
an imager disposed on an image side of the image forming optical system, the imager having a light-receiving surface which is curved to be concave toward the image forming optical system, and the imager outputting an image signal based on light received on the light-receiving surface, wherein a positive lens is disposed between the aperture stop and the diffracting optical surface.

13. An image pickup apparatus, comprising:
an image forming optical system which includes:
an aperture stop that sets an axial light beam; and
a diffracting optical surface disposed at a position different from a position where the aperture stop is disposed, the diffracting optical surface having a relief pattern formed to be rotationally symmetric about an optical axis of the image forming optical system; and
an imager disposed on an image side of the image forming optical system, the imager having a light-receiving surface which is not flat and is curved to be concave toward the image forming optical system, and the imager outputting an image signal based on light received on the light-receiving surface, wherein the diffracting optical surface is formed to be concave toward the aperture stop, wherein the image pickup apparatus satisfies the following conditional expression (2)

$$0.1 < |f/R_{doe}| < 0.8 \qquad (2)$$

where, f denotes a focal length of the image forming optical system, $R_{doe}$ denotes a radius of curvature of a virtual spherical surface including a surface apex and a point at which a principal light ray with a maximum image height of the image forming optical system and the diffracting optical surface intersect, when a point of intersection of the optical axis and the diffracting optical surface is let to be the surface apex, and when the focal length of the image forming optical system is variable, conditional expression (2) is a conditional expression in a state at a wide angle end.

\* \* \* \* \*